(12) United States Patent
Sakaguchi et al.

(10) Patent No.: US 11,672,881 B2
(45) Date of Patent: Jun. 13, 2023

(54) PURIFYING METHOD, PURIFYING DEVICE, AND PURIFYING SYSTEM

(71) Applicant: Panasonic Intellectual Property Management Co., Ltd., Osaka (JP)

(72) Inventors: Yoshihiro Sakaguchi, Hyogo (JP); Hiroko Ikeshima, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 354 days.

(21) Appl. No.: 16/984,198

(22) Filed: Aug. 4, 2020

(65) Prior Publication Data

US 2020/0360554 A1   Nov. 19, 2020

Related U.S. Application Data

(63) Continuation of application No. PCT/JP2019/004692, filed on Feb. 8, 2019.

(30) Foreign Application Priority Data

Mar. 1, 2018 (JP) .............................. JP2018-036705
Jan. 31, 2019 (JP) .............................. JP2019-015583

(51) Int. Cl.
  *A61L 2/24* (2006.01)
  *A61L 2/20* (2006.01)
  *G01N 21/64* (2006.01)

(52) U.S. Cl.
  CPC .................................... *A61L 2/24* (2013.01); *A61L 2/20* (2013.01); *G01N 21/64* (2013.01);
  (Continued)

(58) Field of Classification Search
  CPC ..... A61L 2/24; A61L 2/20; A61L 2/16; A61L 2202/14; G01N 21/64; G01N 21/6486;
  (Continued)

(56) References Cited

U.S. PATENT DOCUMENTS

2010/0303671 A1   12/2010   Bertrand

FOREIGN PATENT DOCUMENTS

CN   102798621 A   11/2012
CN   205569371 U   9/2016
(Continued)

OTHER PUBLICATIONS

Arakeri J.H. et al., "Vortex Ring Formation at the open end of a shock tube: A particle image velocimetry study", Physics of Fluids, vol. 16, No. 4, pp. 1008-1019 (Year: 2004).*
(Continued)

*Primary Examiner* — Jennifer Wecker
*Assistant Examiner* — Brady C Pilsbury
(74) *Attorney, Agent, or Firm* — McDermott Will & Emery LLP

(57) ABSTRACT

A purifying method includes: illuminating a measurement area with excitation light; detecting fluorescence from the measurement area; measuring an amount of amino acids included in the measurement area, based on an intensity of the fluorescence; and discharging a chemical agent to the measurement area, when the amount of amino acids exceeds a first threshold.

13 Claims, 15 Drawing Sheets

(52) U.S. Cl.
CPC .... *A61L 2202/14* (2013.01); *G01N 2201/062* (2013.01); *G01N 2201/06113* (2013.01)

(58) Field of Classification Search
CPC ......... G01N 21/94; G01N 2201/06113; G01N 2201/062; G01N 33/582; G01N 33/6806
See application file for complete search history.

(56) References Cited

FOREIGN PATENT DOCUMENTS

| | | |
|---|---|---|
| CN | 107485725 A | 12/2017 |
| JP | 9-313927 | 12/1997 |
| JP | 2001-062231 | 3/2001 |
| JP | 2008-188189 | 8/2008 |
| JP | 2008-260536 | 10/2008 |
| JP | 2013-022015 | 2/2013 |

OTHER PUBLICATIONS

English Translation of Chinese Search Report dated Oct. 22, 2021 for the related Chinese Patent Application No. 201980005297.1.
International Search Report of PCT application No. PCT/JP2019/004692 dated Apr. 16, 2019.
English Translation of Chinese Search Report dated Jun. 8, 2022 for the related Chinese Patent Application No. 201980005297.1.

* cited by examiner

| TIME POINT | CONTAMINATION-DEGREE LEVEL | SHOOTING CONTROL INFORMATION |
|---|---|---|
| T1 | 5 | LEVEL 1 |
| T2 | 25 | LEVEL 3 |
| T3 | 15 | LEVEL 2 |
| T4 | 2 | SUSPEND |

| RANGE OF CONTAMINATION-DEGREE LEVEL | SHOOTING CONTROL INFORMATION | SHOOTING CONTROL PARAMETERS | | |
|---|---|---|---|---|
| | | NUMBER OF SHOOTS | CONCENTRATION | GAS VOLUME |
| LESS THAN 5 | SUSPEND | 0 | 0 | 0 |
| 5 TO LESS THAN 10 | LEVEL 1 | SMALL | LOW | SMALL |
| 10 TO LESS THAN 20 | LEVEL 2 | MEDIUM | MEDIUM | MEDIUM |
| 20 TO LESS THAN 30 | LEVEL 3 | LARGE | HIGH | LARGE |
| 30 OR MORE | EMERGENCY OPERATION | MAXIMUM | MAXIMUM | MAXIMUM |

PURIFYING METHOD, PURIFYING DEVICE, AND PURIFYING SYSTEM

BACKGROUND

1. Technical Field

The present disclosure relates to a purifying method, a purifying device, and a purifying system.

2. Description of the Related Art

For example, Japanese Unexamined Patent Application Publication No. 2008-188189 discloses a technique utilizing a vortex ring generating apparatus in order to transport gas or minute liquid components to a target place in a room with an intended concentration.

SUMMARY

In one general aspect, the techniques disclosed here feature a purifying method including: illuminating a measurement area with excitation light; detecting fluorescence from the measurement area; measuring an amount of amino acids included in the measurement area, based on an intensity of the fluorescence; and discharging a chemical agent to the measurement area, when the amount of amino acids exceeds a first threshold.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a table illustrating one example of contamination-degree information stored in a storage in the purifying device according to the first embodiment;

FIG. 5 is a table illustrating one example of correspondence information stored in the storage in the purifying device according to the first embodiment;

DETAILED DESCRIPTION (Overview of Present Disclosure)

Figure 1:
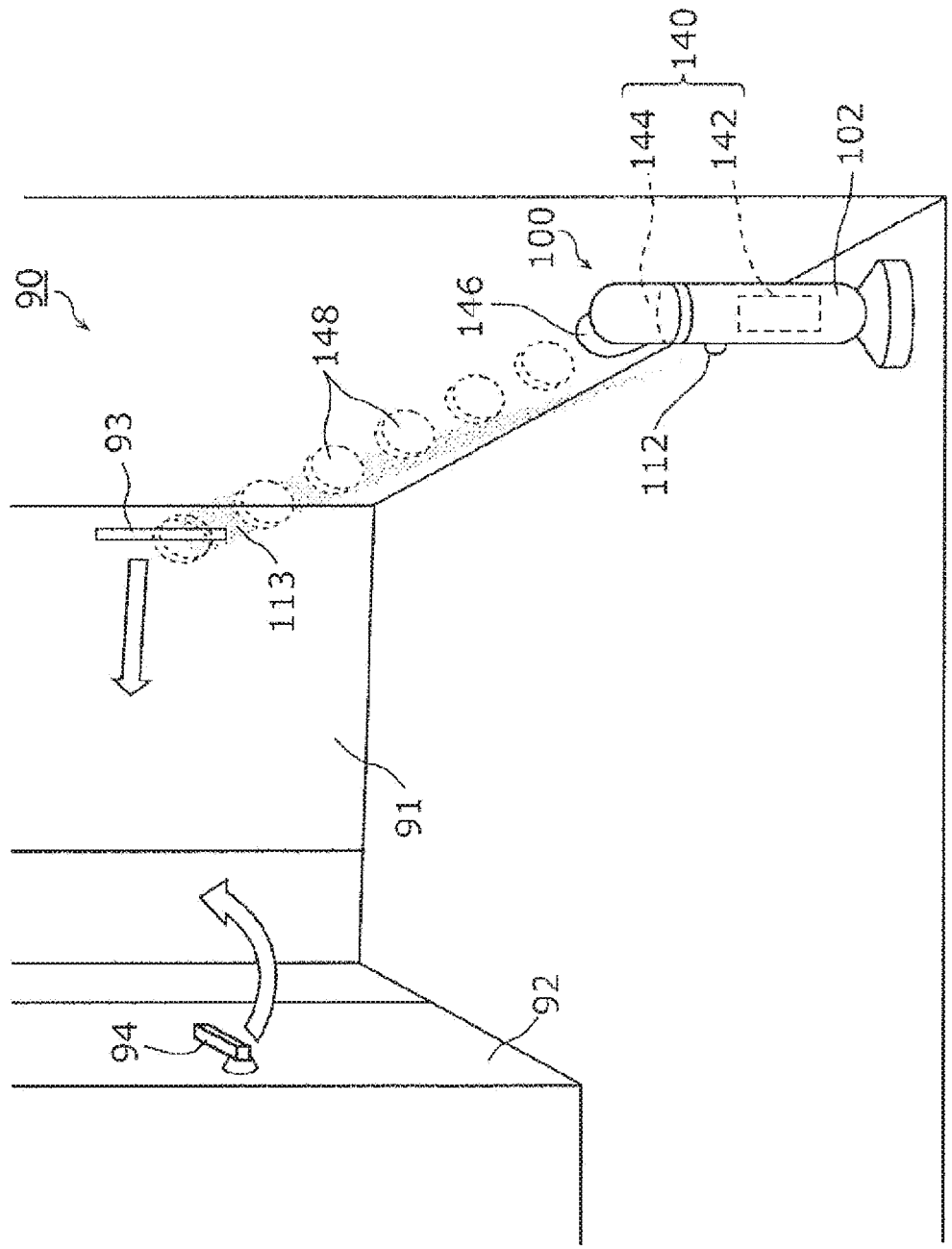
FIG. 1 is a view illustrating an overview of a purifying system according to a first embodiment.

A purifying method according to one aspect of the present disclosure includes: illuminating a measurement area with excitation light; detecting fluorescence from the measurement area; measuring an amount of amino acids included in the measurement area, based on an intensity of the fluorescence; and discharging a chemical agent to the measurement area, when the amount of amino acids exceeds a first threshold. A purifying method according to one aspect of the present disclosure includes: illuminating a measurement area with excitation light; detecting fluorescence from the measurement area; measuring an amount of amino acids included in the measurement area, based on an intensity of the fluorescence; and discharging a chemical agent to the measurement area, after the amount of amino acids exceeds a first threshold.

When germs or viruses are present in the measurement area, amino acids that make up the germs or viruses emit fluorescence when the measurement area is illuminated with the excitation light. Thus, when the amount of amino acids exceeds the first threshold, it is possible to estimate that germs or viruses are present in the measurement area. Accordingly, in the purifying method according to this aspect, when the amount of amino acids exceeds the first threshold, the chemical agent is discharged to the measurement area, thus making it possible to efficiently purify the measurement area, which is a target position to be purified. Also, for example, when the amount of amino acids is smaller than or equal to the first threshold, the purifying method can disable the discharging of the chemical agent, thus making it possible to reduce waste of the chemical agent.

Also, for example, the purifying method may further include: obtaining a contamination-degree level corresponding to the amount of amino acids included in the measurement area, after measuring the amount of amino acids. In the discharging of the chemical agent, when the contamination-degree level exceeds a second threshold, the chemical agent may be discharged to the measurement area, based on at least one shooting control parameter determined based on the contamination-degree level. In the discharging of the chemical agent, after the contamination-degree level exceeds a second threshold, the chemical agent may be discharged to the measurement area, based on at least one shooting control parameter determined based on the contamination-degree level.

Examples of a case in which the contamination-degree level exceeds the second threshold includes cases in which immediate purification is needed, such as a case in which infection of a disease is highly likely to spread. Thus, when the contamination-degree level exceeds the second threshold, the chemical agent is shot based on the at least one shooting control parameter determined based on the contamination-degree level, thus making it possible to purify the measurement area.

Also, for example, in the discharging of the chemical agent, the at least one shooting control parameter may be determined by referring to correspondence information in which contamination-degree levels and shooting control parameters are associated with each other.

With this arrangement, since the correspondence information is prepared, it is not necessary to perform complicated arithmetic operation to determine the at least one shooting control parameter. This makes it possible to reduce the amount of arithmetic operation and makes it possible to reduce power consumed for the arithmetic operation.

For example, the purifying method may further include obtaining an instruction for purifying the measurement area, before the chemical agent is discharged.

With this arrangement, since the chemical agent is discharged when the instruction is obtained, for example, the discharge of the chemical agent can be reduced when no purification is needed.

Also, for example, after the instruction is obtained, the discharging of the chemical agent may be suspended when the amount of amino acids is smaller than or equal to the first threshold. The discharging of the chemical agent may be suspended after the amount of amino acids is confirmed to be smaller than or equal to the first threshold.

When the amount of amino acids is smaller than or equal to the first threshold, it is possible to estimate that germs or viruses are not present in the measurement area. That is, when the amount of amino acids is smaller than or equal to the first threshold, it is possible to estimate that the measurement area does not need to be purified. Thus, in the purifying method according to this aspect, since the shooting of the chemical agent is suspended even when the instruction is obtained, it is possible to reduce waste of the chemical agent.

Also, for example, in the discharging of the chemical agent, a vortex ring formed of gas containing the chemical agent may be shot to the measurement area.

This allows the chemical agent to efficiently reach the target position via the vortex ring. For example, of the chemical agent that is shot, the amount of the chemical agent that spreads and does not reach the target position can be reduced, thus making it possible to reduce waste of the chemical agent.

Also, for example, in the discharging of the chemical agent, a vortex ring formed of gas containing the chemical agent may be shot to the measurement area; and the at least one shooting control parameter may include at least one selected from the group consisting of the number of shoots of the vortex ring, a gas volume of the vortex ring, and a concentration of the chemical agent.

This allows the chemical agent to efficiently reach the target position via the vortex ring. For example, of the chemical agent that is shot, the amount of the chemical agent that spreads and does not reach the target position can be reduced, thus making it possible to reduce waste of the chemical agent. In addition, since the number of shoots of the vortex ring, the gas volume of the vortex ring, or the concentration of the chemical agent can be adjusted, an appropriate amount of the chemical agent can be made to reach the measurement area in accordance with the contamination-degree level.

Also, for example, the measurement area may be a doorknob or a trace of wiped vomit.

This makes it possible to efficiently purify a doorknob that can be a contact infection source when it is touched by a large number of people and a trace of wiped vomit in which germs or viruses are highly likely to be present.

For example, a diameter of a range in which the discharged chemical agent contacts the measurement area may be 5 cm or more and 50 cm or less.

With this arrangement, since the chemical agent is shot in a localized manner, it is possible to reduce the chemical agent spreading to a range that does not need to be purified and makes it possible to reduce waste of the chemical agent.

For example, in the measuring of the amount of amino acids, the amount of amino acids may be measured based on a combination of a wavelength of the excitation light and a wavelength of the fluorescence.

This makes it possible to utilize excitation emission matrix (EEM) information and makes it possible to increase the accuracy of detecting the amino acids. Accordingly, since the accuracy of determining whether or not the purification is needed can also be increased, thus making it possible to efficiently use the chemical agent.

For example, the purifying method may further include monitoring a user's contact operation on an object included in the measurement area. In the measuring of the amount of amino acids, after the user finishes the contact operation, the amount of amino acids in the measurement area may be measured.

When the user touches an object that is present in the measurement area, there is a possibility that germs or viruses adhere to the object. According to the purifying method according to this aspect, when a user's contact operation is detected, the amount of amino acids is measured to thereby effectively purify the measurement area.

Also, for example, a purifying method according to one aspect of the present disclosure may include: sequentially executing recording processes, each of which includes illuminating a measurement area with excitation light, detecting fluorescence from the measurement area, measuring an amount of amino acids in the measurement area based on an intensity of the fluorescence, obtaining a contamination-degree level corresponding to the amount of amino acids, and recording at least one shooting control parameter corresponding to the obtained contamination-degree level to a storage by using correspondence information in which contamination-degree levels and shooting control parameters for a chemical agent are associated with each other; obtaining an instruction for purifying the measurement area; and discharging, after obtaining the instruction, the chemical agent to the measurement area in accordance with the at least one shooting control parameter recorded in the recording process most recently executed in the recording processes.

With this arrangement, since the at least one shooting control parameter is sequentially stored in the storage, the measurement area can be purified immediately when the instruction for the purification is obtained. Also, since the at least one shooting control parameter is determined based on the contamination-degree level, an appropriate amount of chemical agent corresponding to the contamination-degree level of the measurement area can be made to reach the measurement area. Accordingly, the purifying method according to this aspect makes it possible to efficiently purify the measurement area, which is a target position to be purified.

Also, for example, in the discharging of the chemical agent, when the contamination-degree level obtained before the instruction is obtained exceeds a threshold, the chemical agent may be discharged to the measurement area in accordance with the at least one shooting control parameter recorded in the recording process most recently executed in the recording processes. After the contamination-degree level obtained before the instruction is obtained exceeds a threshold, the chemical agent may be discharged to the measurement area in accordance with the at least one shooting control parameter recorded in the recording process most recently executed in the recording processes.

Examples of a case in which contamination-degree level exceeds the threshold include cases in which immediate purification is needed, such as a case in which infection of a disease is highly likely to spread. Thus, when the contamination-degree level exceeds the threshold, the chemical agent is shot based on the at least one shooting control parameter determined based on the contamination-degree level, thus making it possible to purify the measurement area.

Also, for example, a purifying device according to one aspect of the present disclosure may include: a discharger that includes a container for storing a chemical agent and that discharges the chemical agent stored in the container; and a controller that controls the discharger. The controller may cause the discharger to discharge the chemical agent to a measurement area when an amount of amino acids included in the measurement area exceeds a threshold, the amount of amino acids being measured by a sensor that illuminates the measurement area with excitation light, that detects fluorescence from the measurement area, and that measures the amount of amino acids based on an intensity of the fluorescence.

Thus, as in the purifying method described above, the chemical agent is discharged to the measurement area when the amount of amino acids exceeds the threshold, thus making it possible to efficiently purify the measurement area, which is a target position to be purified.

Also, for example, a purifying device according to one aspect of the present disclosure may include: a discharger that includes a container for storing a chemical agent and that discharges the chemical agent stored in the container; a controller that controls the discharger and a storage. The controller may sequentially execute recording processes, in each of which the controller obtains a contamination-degree level corresponding to an amount of amino acids included in a measurement area and records at least one shooting control parameter corresponding to the contamination-degree level to the storage by using correspondence information in which contamination-degree levels and shooting control parameters for the chemical agent are associated with each other, the amount of amino acids being measured by a sensor that illuminates the measurement area with excitation light, that detects fluorescence from the measurement area, and that measures the amount of amino acids based on an intensity of the fluorescence; obtains an instruction for purifying the measurement area; and discharges, after obtaining the instruction, the chemical agent to the measurement area in accordance with the at least one shooting control parameter recorded in the recording process most recently executed in the recording processes.

This makes it possible to efficiently purify the measurement area, which is a target position to be purified, as in the purifying method described above.

For example, the sensor may be separated from the purifying device.

For example, the purifying system according to one aspect of the present disclosure may include the purifying device according to the aspect described above and the sensor according to the aspect described above.

This makes it possible to efficiently purify the measurement area, which is a target position to be purified, as in the purifying device described above.

For example, a purifying device according to one aspect of the present disclosure may include: a storage for storing a contamination-degree level of a target position, the contamination-degree level being detected by a sensor, or at least one shooting control parameter determined based on the contamination-degree level; a purifying unit that shoots a chemical agent to the target position in a localized manner; and a controller. Upon obtaining a purification instruction, the controller shoots the chemical agent, based on the at least one shooting control parameter.

With this arrangement, since the chemical agent is shot based on the at least one shooting control parameter determined based on the contamination-degree level, an appropriate amount of the chemical agent can be made to reach the target position in accordance with the contamination-degree level of the target position, thus making it possible to efficiently purify the target position. For example, in the purifying device according to this aspect, when the contamination-degree level is high, the amount of the chemical agent to be shot is increased, and when the contamination-degree level is low, the amount of the chemical agent to be shot is reduced. Since an excess or shortage of the chemical agent can be reduced as described above, it is possible to efficiently purify the target position while reducing waste of the chemical agent.

For example, upon obtaining the contamination-degree level from the sensor, the controller may compare the obtained contamination-degree level with a predetermined second threshold, and when the obtained contamination-degree level is larger than or equal to the second threshold, the controller may shoot the chemical agent.

The second threshold is, for example, a threshold for determining whether or not the contamination-degree level is high to a degree that purification is to be immediately performed since there is a risk of spread of disease infection. Thus, when the contamination-degree level is so high, it is possible to shoot the chemical agent without waiting for obtaining the purification instruction. Accordingly, it is possible to prevent or reduce spread of disease infection due to contamination.

For example, when correspondence information in which predetermined shooting control parameters associated with ranges of contamination-degree levels are stored in the storage, and the controller obtains the contamination-degree level from the sensor, the controller may determine at least one shooting control parameter corresponding to the contamination-degree level by referring to the correspondence information.

This allows the at least one shooting control parameter to be determined by merely referring to the correspondence information on the basis of the contamination-degree level, thus making it possible to reduce the arithmetic operation involved for shooting the chemical agent. The correspondence information may also be updated depending on the environment or the like, and it is possible to purify the target position with an appropriate condition while adapting to changes in the environment or the like.

For example, when the controller obtains the purification instruction, and the contamination-degree level stored in the storage is smaller than or equal to a predetermined threshold, the controller may suspend the shooting of the chemical agent.

Thus, when the contamination-degree level is sufficiently low, the shooting of the chemical agent can be suspended even when the purification instruction is obtained. Accordingly, it is possible to efficiently purify the target position when needed, while reducing waste of the chemical agent.

Also, for example, the purifying unit may shoot a vortex ring formed of gas containing the chemical agent to the target position.

With this arrangement, since the vortex ring is shot, the chemical agent can be efficiently transported to the target position via the vortex ring. Accordingly, a sufficient amount of the chemical agent can be transported to the target position, thus making it possible to efficiently purify the target position.

Also, for example, the at least one shooting control parameter may include at least one of the number of shoots of the vortex ring, a concentration of the chemical agent, and a gas volume of the vortex ring.

Thus, for example, when the contamination-degree level is high, it is possible to increase the amount of chemical agent that reaches the target position, by increasing at least one of the number of shoots, the concentration, and the gas volume. Also, for example, when the contamination-degree level is low, it is possible to reduce the amount of chemical agent that reaches the target position, by reducing at least one of the number of shoots, the concentration, and the gas volume. Since an excess or shortage of the chemical agent can be reduced as described above, it is possible to efficiently purify the target position while reducing waste of the chemical agent.

Also, a purifying system according to one aspect of the present disclosure includes the purifying device according to each aspect described above and the sensor according to each aspect described above.

This makes it possible to efficiently purify the target position, as in the purifying device described above.

Also, for example, the contamination-degree level of the target position which is detected by the sensor or the at least one shooting control parameter determined based on the contamination-degree level may be stored in the storage, and when the purification instruction is obtained, the chemical agent may be shot in a localized manner to the target position, based on the at least one shooting control parameter.

This makes it possible to efficiently purify the target position, as in the purifying device described above.

In the present disclosure, all or a part of any of circuits, units, apparatuses, devices, parts, or portions or all or a part of functional blocks in the block diagrams may be implemented as one or more of electronic circuits including, but not limited to, a semiconductor device, a semiconductor integrated circuit (IC), or a large-scale integration (LSI). The LSI or IC can be integrated into one chip or also may be a combination of a plurality of chips. For example, functional blocks other than a memory may be integrated into one chip. Although the name used here is an LSI or IC, it may also be called a system LSI, a very large-scale integration (VLSI), or an ultra-large-scale integration (ULSI) depending on the degree of integration. A field programmable gate array (FPGA) that can be programmed after manufacturing an LSI or a reconfigurable logic device that allows reconfiguration of the connection or setup of circuit cells inside the LSI can also be used for the same purpose.

In addition, the functions or operations of all or a part of the circuits, units, apparatuses, devices, parts, or portions can be implemented by executing software. In such a case, the software is recorded on one or more non-transitory storage media, such as a ROM, an optical disk, or a hard disk drive, and when the software is executed by a processor, the software causes the processor together with peripheral devices to execute the functions specified in the software. A system, an apparatus, or a device may include such one or more non-transitory storage media on which the software is recorded and a processor together with necessary hardware devices such as an interface.

Embodiments will be described below in detail with reference to the accompanying drawings.

The embodiments described below each present a general or specific example. Numerical values, shapes, materials, constituent elements, the arrangement positions and connections of constituent elements, steps, the order of steps, and so on described in the embodiments below are merely examples and are not intended to limit the present disclosure. Also, of the constituent elements in the embodiments below, constituent elements not set forth in the independent claims will be described as optional constituent elements.

That is, the drawings are schematic diagrams and are not necessarily strictly illustrated. Accordingly, for example, scales and so on do not necessarily match in each drawing. In each drawing, substantially the same constituent elements are denoted by the same reference numerals, and redundant descriptions are not given or are briefly given.

First Embodiment

[Overview]

First, an overview of a purifying system according to a first embodiment will be described with reference to FIG. 1. FIG. 1 is a view illustrating an overview of a purifying system 100 according to the present embodiment.

The purifying system 100 is a system for purifying a predetermined place in a predetermined space, such as a room, by using a chemical agent shot by a purifying device 102. FIG. 1 illustrates a space 90 including a place that is to be purified by the purifying device 102.

The space 90 is, for example, one room in a building, such as a care facility or a hospital. The space 90 is, for example, a closed space bounded by walls, windows, doors, a floor, a ceiling, and so on, but is not limited thereto. The space 90 may be an outdoor open space. The space 90 may also be an internal space of a moving object, such as a bus or an airplane.

As illustrated in FIG. 1, the space 90 has doors 91 and 92. Each of the doors 91 and door 92 can be freely opened or closed from the inside and outside of the space 90.

The door 91 is a sliding door and is provided with a handle 93. The handle 93 is, for example, an elongated rod-shaped member that is easily grasped by a person and is secured to a surface of a door plate of the door 91. Alternatively, the handle 93 may be a depression portion that is provided in the door plate of the door 91 and that is depressed to such a degree that a person's fingertip can be put thereinto.

A person can open or close the door 91 by putting his or her hand on the handle 93 and sliding the door 91 to the side. In FIG. 1, a hollow straight arrow depicted near the handle 93 indicates a direction in which the door 91 is opened. The shape, the installation position, and so on of the handle 93 are not particularly limiting.

The door 92 is a swing door and is provided with a doorknob 94. At least a part of the doorknob 94 is provided pivotally. The human can open or close the door 92 by turning the doorknob 94 and pulling it toward him or her or pushing it away from him or her. In FIG. 1, a hollow curved arrow depicted near the doorknob 94 indicates a direction in which the door 92 is opened. The shape, the installation position, and so on of the doorknob 94 are not particularly limiting.

In the present embodiment, the handle 93 and the doorknob 94 are target positions that are to be purified. That is, each of the handle 93 and the doorknob 94 is located at a position that is to be reached by the chemical agent shot by the purifying device 102.

The handle 93 and the doorknob 94 are generally portions that a large number of people touch when opening or closing the doors 91 and 92. Thus, when pathogens, such as viruses or germs, adhere to the handle 93 and the doorknob 94, this can lead to spread of disease infection. Thus, in the purifying system 100 according to the present embodiment, the handle 93 and the doorknob 94 are target positions to be purified. The target positions are measurement areas in which the amount of amino acids is to be measured. Since amino acids are substances that make up germs or viruses, a determination as to whether or not the chemical agent is to be shot is made based on the amount of amino acids.

The target positions are not limited to the handle 93 and the doorknob 94. Examples of the target positions include an operation terminal for household electrical or electronic equipment that is present in the space 90, a trace of wiped vomit of a person, and so on.

In the present embodiment, the purifying device 102 is placed in the space 90. The entire purifying device 102 does not have to be placed in the space 90, and for example, only a shooting port 146 for the chemical agent may be located in the space 90. The purifying device 102 is secured to a predetermined position in the space 90.

The purifying device 102 is a device that shoots the chemical agent in a localized manner to a target position. Since the purifying device 102 shoots the chemical agent in a localized manner, it is possible to reduce the chemical agent reaching a range in which purification is not needed, thus making it possible to reduce waste of the chemical agent.

The "shooting in a localized manner" as used herein means shooting the chemical agent to only within a predetermined range centered in a predetermined shooting direction, rather than spraying the chemical agent so that it spreads throughout the space 90. That is, the shooting direction of the chemical agent has directivity. For example, the diameter of the range in which the chemical agent reaches at the target position is in the range of a few centimeters to 100 cm. For example, the range of the diameter may be 5 to 50 cm.

In the present embodiment, the purifying device 102 shoots a vortex ring 148 formed of gas containing the chemical agent to a target position. That is, the chemical agent is transported to the target position in an airborne manner.

The chemical agent is, for example, a liquid for purifying and detoxing microorganisms, such as viruses or germs. Specifically, the chemical agent is hypochlorous acid water, a sodium hypochlorite formulation, an alcohol formulation, or the like. The chemical agent does not necessarily have to be a liquid and may be a gas or solid.

A contamination-degree level of a target position differs depending on the situation. For example, even when a healthy person touches the handle 93, the handle 93 is scarcely contaminated. On the other hand, when a diseased person touches the handle 93, viruses or germs that have adhered to his or her hand may adhere to the handle 93. Thus, the contamination-degree level of the handle 93 varies depending on the situation. Also, when there is a plurality of target positions, the contamination-degree levels of the target positions also may differ from each other.

The "contamination-degree level" as used herein refers to a measure indicating the contamination degree of a target position. Specifically, the contamination-degree level indicates the amount of viruses or germs that have adhered to a target position or an output value of a sensor for detecting the amount of viruses or germs. In the present embodiment, a higher contamination-degree level means that, for example, the amount of viruses or germs that have adhered to a target position is larger, and the target position is more contaminated. A lower contamination-degree level means that, for example, the amount of viruses or germs that have adhered to a target position is smaller, and the target position is less contaminated.

[Configuration]

Next, the configuration of the purifying system 100 according to the present embodiment will be described with reference to FIG. 2.

Figure 2:
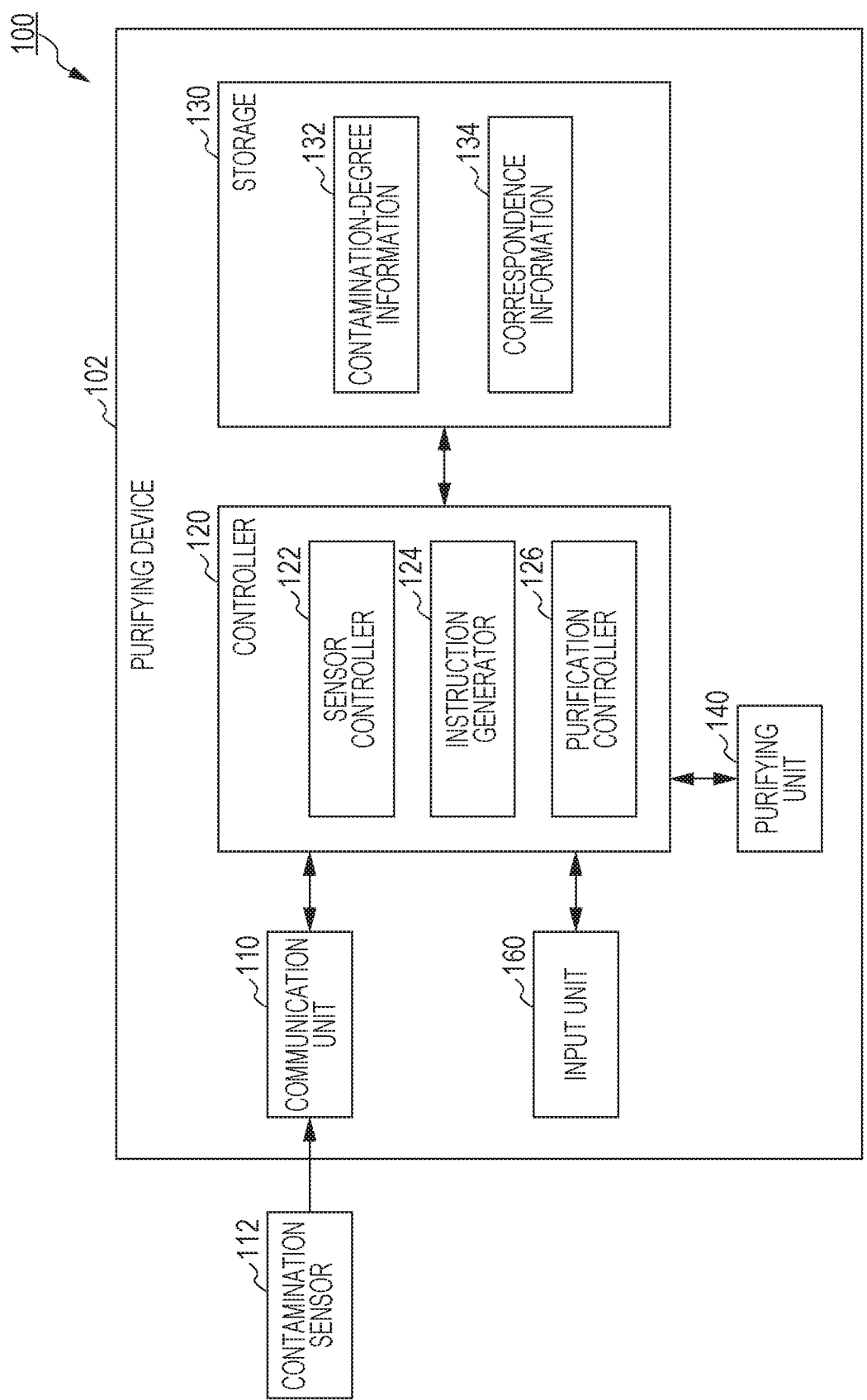
FIG. 2 is a block diagram illustrating the configuration of the purifying system according to the first embodiment.

FIG. 2 is a block diagram illustrating the configuration of the purifying system 100 according to the present embodiment. As illustrated in FIG. 2, the purifying system 100 includes a purifying device 102 and a contamination sensor 112.

The contamination sensor 112 is a sensor for detecting the contamination-degree level of a target position to be purified. Specifically, the contamination sensor 112 detects organics, such as viruses or germs, included in a target position and outputs the amount of detected organics as the contamination-degree level. In the present embodiment, the contamination sensor 112 detects the contamination-degree level by measuring the amount of amino acids. The contamination sensor 112 may output a measurement value indicating the measured amount of amino acids to the purifying device 102. In this case, based on the amount of amino acids, the purifying device 102 may determine the contamination-degree level.

In the present embodiment, the contamination sensor 112 measures the amount of amino acids, based on a combination of the wavelength of excitation light and the wavelength of received fluorescence and the intensity of the fluorescence. For example, the contamination sensor 112 optically measures the amount of amino acids by utilizing the so-called fluorescent fingerprint and detects the contamination-degree level on the basis of the measured amount of amino acids. The fluorescent fingerprint is excitation-emission matrix (EEM) information. The fluorescent fingerprint is three-dimensional data whose three axes are the wavelength of the excitation light, the wavelength of the fluorescence, and the intensity of the fluorescence.

For example, when amino acids and so on that make up viruses or germs are illuminated with excitation light having its peak at about 280 nm, they emit fluorescence having its peak at about 320 nm. Thus, the presence/absence of amino acids, that is, the presence/absence of viruses or germs, can be determined based on a combination of the wavelength of the excitation light and the wavelength of the fluorescence.

Also, the amount of amino acids, that is, the amount of viruses or germs, can be determined according to the intensity of fluorescence.

Figure 3:
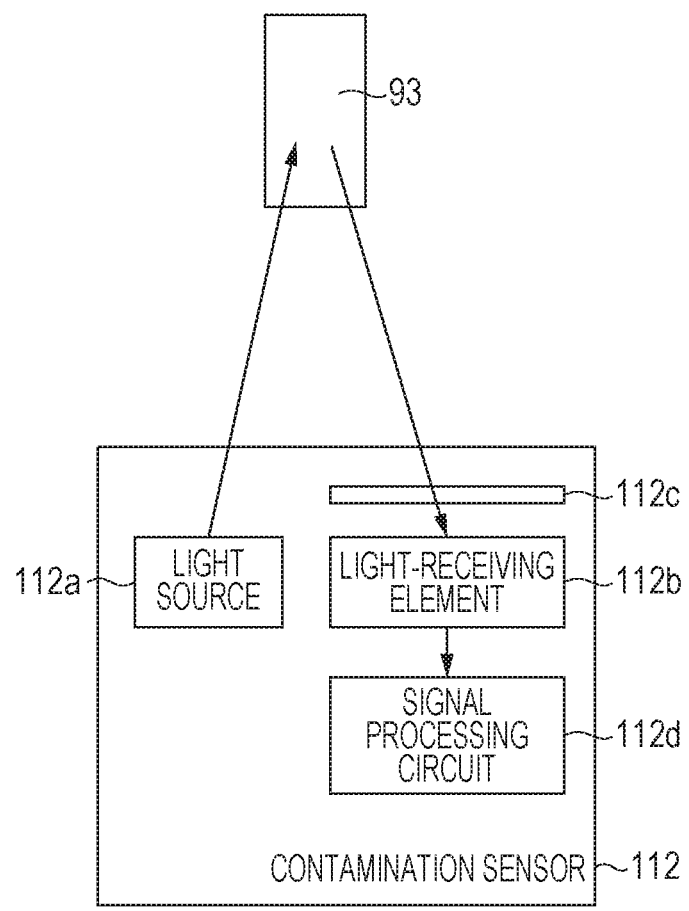
FIG. 3 is a block diagram illustrating the configuration of a contamination sensor included in the purifying system according to the first embodiment.

FIG. 3 is a block diagram illustrating the configuration of the contamination sensor 112 included in the purifying system 100 according to the present embodiment. FIG. 3 schematically illustrates an example in which the contamination sensor 112 measures the amount of amino acids on the handle 93 of the door 91, the handle 93 being a measurement area. As illustrated in FIG. 3, the contamination sensor 112 includes a light source 112a, a light-receiving element 112b, a spectroscopic element 112c, and a signal processing circuit 112d.

The light source 112a emits the excitation light. The excitation light is light for causing fluorescence to be generated from amino acids present in the measurement area when the measurement area is illuminated with the excitation light. The amino acids are one example of organics and are included in germs or viruses.

The light source 112a is, for example, a solid light-emitting element, such as a semiconductor laser or a light-emitting diode (LED), or a discharge lamp, such as a halogen lamp. The light source 112a may have a spectroscopic element provided at its light-emitting side and may emit light with a particular wavelength band as the excitation light. The wavelength of the excitation light is, for example, in the range of 220 to 550 nm, but is not limited thereto. The excitation light is, for example, ultraviolet light having a wavelength of 250 to 350 nm. The excitation light is pulsed light or may be continuous light. The light source 112a illuminates, for example, excitation light having its peak at about 280 nm.

The light-receiving element 112b receives fluorescence that is emitted from amino acids when they are illuminated with the excitation light. The light-receiving element 112b is, for example, a photomultiplier tube (PMT) or an avalanche photodiode. The light-receiving element 112b may have a photon counter. The light-receiving element 112b outputs, to the signal processing circuit 112d, an electrical signal corresponding to the intensity of the received fluorescence. The wavelength of the fluorescence is longer than the wavelength of the excitation light and is, for example, in the range of 250 to 1000 nm, but is not limited thereto. For example, the fluorescence is ultraviolet light and has a wavelength of 270 to 330 nm. The light-receiving element 112b can, for example, selectively receive light of about 320 nm.

The spectroscopic element 112c splits incident light into particular wavelengths. The spectroscopic element 112c is provided at the light-incident side of the light-receiving element 112b to allow the light-receiving element 112b to receive light having a particular wavelength. The particular wavelength is, for example, a wavelength that is specific to substances to be detected. For example, when substances to be detected are amino acids, the particular wavelength is 270 nm to 330 nm. The spectroscopic element 112c is, for example, a diffraction grating, a prism, or a band-pass filter. The contamination sensor 112 may or may not include the spectroscopic element 112c.

The signal processing circuit 112d processes the electrical signal output from the light-receiving element 112b. The signal processing circuit 112d is implemented by, for example, a processor or one or more electronic circuits. One or more electronic circuits may be general-purpose circuits or dedicated circuits.

The signal processing circuit 112d processes the electrical signal to detect the amount of amino acids from which the fluorescence is generated and the position of the amino acids. Specifically, the signal processing circuit 112d calculates the amount of amino acids, based on the intensity of the fluorescence. For example, the signal processing circuit 112d stores, in a memory, a function or a correspondence table indicating a relationship between the signal level of the electrical signal and the amount of amino acids. By performing arithmetic operation using the function or by referring to the correspondence table, the signal processing circuit 112d determines the amount of amino acids, based on the signal level of the electrical signal. The signal level is, for example, a voltage value or a current value of the electrical signal and corresponds to the intensity of the fluorescence received by the light-receiving element 112b.

Also, by using the direction in which the excitation light is emitted and a time from when the excitation light is emitted until the fluorescence is received, the signal processing circuit 112d calculates the distance from the contamination sensor 112 to the amino acids to thereby detect the position of the amino acids, that is, the position of the measurement area. The contamination sensor 112 outputs, as a sense signal, position information indicating the detected position.

This allows the measurement area to be not only the surface of an object but also be in the air in the space 90 and makes it possible to detect amino acids contained in aerosols floating in the space 90. For example, the aerosols are airborne droplets that are dispersed when a human coughs or sneezes. For example, by scanning the space 90 while changing the emission direction of the excitation light from the light source 112a, the contamination sensor 112 can measure the amount of amino acids that make up germs or viruses contained in the aerosols in the space 90. When the position of the measurement area is a predetermined position, such as the handle 93, the signal processing circuit 112d does not necessarily have to detect the position and output the position information.

Depending on an object to be detected, the contamination sensor 112 may change at least one of the wavelength of the excitation light and a selected wavelength to be received.

The contamination sensor 112 illuminates the target position with the excitation light, receives fluorescence emitted from viruses or germs, present at the target position, when the viruses or germs are illuminated with the excitation light, and performs photoelectric conversion to convert the received fluorescence to generate an electrical signal. Based on the signal strength of the generated electrical signal, the contamination sensor 112 calculates the amount of amino acids corresponding to the amount of viruses or germs.

The contamination sensor 112 outputs a contamination-degree level determined based on the calculated amount of amino acids. For example, the signal processing circuit 112d stores, in the memory, a function or a correspondence table indicating the relationship between the amount of amino acids and the contamination-degree level. By performing arithmetic operation using the function or by referring to the correspondence table, the signal processing circuit 112d determines the contamination-degree level, based on the amount of amino acids. The amount of amino acids may itself be the contamination-degree level.

In the present embodiment, the contamination sensor 112 sequentially executes the measurement of the amount of amino acids and the determination of the contamination-degree level. The time intervals of the measurement and the determination are arbitrary time intervals. That is, the time intervals may be regular time intervals or may be random time intervals.

In the present embodiment, the contamination sensor 112 is a contactless sensor. That is, the contamination sensor 112 detects the contamination-degree level of a target position that is away from the sensor. The contamination sensor 112 may have a filter for reducing noise components due to an illumination light and so on placed in the space 90.

In FIG. 1, the emission range of the excitation light from the contamination sensor 112, that is, a detection range 113 of the contamination-degree level, is schematically depicted by dotted shading. The contamination sensor 112 receives fluorescence from viruses or germs that are present in the detection range 113. When there is a plurality of target positions, the contamination sensor 112 changes the detection range 113 for each target position. Alternatively, the purifying system 100 may include a plurality of contamination sensors 112. For example, the plurality of contamination sensors 112 may detect contamination-degree levels of respective target positions.

In the present embodiment, one contamination sensor 112 is integrated with the purifying device 102, as illustrated in FIG. 1. Alternatively, the contamination sensor(s) 112 may be provided independently from the purifying device 102. For example, the contamination sensor(s) 112 may be provided on any of the walls and ceiling that define the space 90. The contamination sensor 112 may be provided adjacent to a target position. Each contamination sensor 112 communicates with a communication unit 110 in the purifying device 102 to thereby output the contamination-degree level to the purifying device 102.

As illustrated in FIG. 2, the purifying device 102 includes the communication unit 110, a controller 120, a storage 130, a purifying unit 140, and an input unit 160.

The communication unit 110 communicates with each contamination sensor 112 in a wired or wireless manner. For example, the communication unit 110 performs wireless communication that complies with a wireless communication standard, such as a Wi-Fi®, Bluetooth®, or ZigBee® standard. The communication unit 110 obtains the contamination-degree level from the contamination sensor 112. The obtained contamination-degree level is output to a sensor controller 122 in the controller 120.

As illustrated in FIG. 2, the controller 120 includes the sensor controller 122, an instruction generator 124, and a purification controller 126. The controller 120 is implemented by, for example, a nonvolatile memory in which a program is stored, a volatile memory that is a temporary storage area for executing the program, input/output ports, and a processor that executes the program. Each of the sensor controller 122, the instruction generator 124, and the purification controller 126 included in the controller 120 may be implemented by software executed by a processor or may be implemented by hardware, such as an electronic circuit including a plurality of circuit elements.

The sensor controller 122 controls operations related to the contamination sensor 112. Specifically, the sensor controller 122 stores, in the storage 130, the contamination-degree level output from the contamination sensor 112. More specifically, the sensor controller 122 stores the contamination-degree level in the storage 130 in association with a detection time point.

The detection time point is a time point at which, for example, the communication unit 110 obtains the contamination-degree level. Alternatively, when the contamination sensor 112 outputs not only the contamination-degree level but also time information indicating a time point at which the contamination-degree level was detected, the detection time point may be a time point indicated by the time information.

In the present embodiment, the sensor controller 122 sequentially executes a plurality of recording processes. In each of the recording processes, the sensor controller 122 obtains a contamination-degree level corresponding to the amount of amino acids measured by the contamination sensor 112 and records shooting control parameters corresponding to the obtained contamination-degree level to the storage 130 by using correspondence information 134 in which contamination-degree levels and the shooting control parameters for the chemical agent are associated with each other. Specifically, upon obtaining the contamination-degree level from the contamination sensor 112, the sensor controller 122 determines shooting control parameters corresponding to the obtained contamination-degree level by referring to the correspondence information 134 stored in the storage 130. The sensor controller 122 stores the determined shooting control parameters in the storage 130. The shooting control parameters include, for example, at least one of the number of shoots of the vortex ring 148, the concentration of the chemical agent, and the gas volume of the vortex ring 148.

The correspondence information 134 is information in which predetermined shooting control parameters are associated with respective ranges of contamination-degree levels. A specific example of the correspondence information 134 is described later with reference to FIG. 5.

Upon obtaining the contamination-degree level from the contamination sensor 112, the sensor controller 122 compares the obtained contamination-degree level with a predetermined second threshold. The second threshold is, for example, a threshold for determining whether or not the contamination degree is high to a degree that purification is to be immediately performed since there is a risk of spread of disease infection. When the obtained contamination-degree level exceeds the second threshold, the sensor controller 122 generates an emergency purification instruction and outputs the emergency purification instruction to the purification controller 126. The sensor controller 122 may output a result of the comparison with the second threshold to the instruction generator 124, or the instruction generator 124 may generate the emergency purification instruction.

The instruction generator 124 generates a purification instruction and outputs the generated purification instruction to the purification controller 126. The purification instruction is an instruction for purifying a measurement area, specifically, an instruction indicating that a target position is to be purified. The purification instruction includes information indicating the target position.

The instruction generator 124 generates the purification instruction, for example, based on predetermined schedule information. The schedule information indicates a timing at which a target position is to be purified, that is, timing at which the chemical agent is to be shot. For example, the schedule information indicates time intervals, such as 30 minutes or 1 hour, at which the chemical agent is to be shot or time points, such as 10:00 and 10:30, at which the chemical agent is to be shot.

Alternatively, the instruction generator 124 may generate the purification instruction, based on a user operation received by the input unit 160. This makes it possible to purify a target position at an arbitrary timing desired by a user. The instruction generator 124 may also generate a purification instruction, based on an instruction obtained from another device via the communication unit 110.

The purification controller 126 controls the purifying unit 140. Specifically, upon obtaining the purification instruction, the purification controller 126 shoots the chemical agent, based on the shooting control parameters determined based on the contamination-degree level stored in the storage 130.

Specifically, upon obtaining the purification instruction, the purification controller 126 reads the shooting control parameters recorded in the recording process most recently executed in the recording processes. For example, upon obtaining the purification instruction, the purification controller 126 reads contamination-degree information 132 and the correspondence information 134 from the storage 130. By referring to the contamination-degree information 132, the purification controller 126 obtains shooting control information associated with a time point that is the closest to the time point at which the purification instruction was obtained. By referring to the correspondence information 134 on the basis of the obtained shooting control information, the purification controller 126 obtains the shooting control parameters. The purification controller 126 controls the purifying unit 140 to shoot the vortex ring 148 in accordance with the number of shoots, the concentration, and the gas volume which are indicated by the shooting control parameters.

The storage 130 is, for example, a nonvolatile storage device, such as a semiconductor memory or a hard disk drive (HDD). As illustrated in FIG. 2, the contamination-degree information 132 and the correspondence information 134 are stored in the storage 130.

As illustrated in FIG. 4, in the contamination-degree information 132, contamination-degree levels obtained by the contamination sensor 112 are associated with detection time points. FIG. 4 is a table illustrating one example of the contamination-degree information 132 stored in the storage 130 in the purifying device 102 according to the present embodiment.

In the present embodiment, in the contamination-degree information 132, pieces of shooting control information are further associated with the detection time points. Each piece of the shooting control information is determined by the sensor controller 122 referring to the correspondence information 134 when the contamination-degree level is obtained from the contamination sensor 112. The shooting control information is then stored in the storage 130. The pieces of shooting control information are associated with shooting control parameters determined based on the contamination-degree levels.

The correspondence information 134 is information in which predetermined shooting control parameters are associated with respective ranges of the contamination-degree levels. Specifically, as illustrated in FIG. 5, in the correspondence information 134, the ranges of the contamination-degree levels, the pieces of shooting control information, and the shooting control parameters are associated with each other.

In the example illustrated in FIG. 5, the contamination-degree levels are divided into the ranges of five stages. The pieces of shooting control information are associated with the ranges of five stages, respectively. In each piece of shooting control information, the number of shoots of the vortex ring 148, the concentration of the chemical agent contained in the vortex ring 148, and the gas volume of the vortex ring 148 are associated with each other as the shooting control parameters.

For example, when the contamination-degree level is lower than "5", suspension of the shooting is associated therewith as the shooting control information. When the contamination-degree level is lower than "5", the chemical agent is not shot even when the purification instruction is obtained.

When the contamination-degree level is in the range of "5" to less than "30", three-stage levels 1 to 3 are associated according to the contamination-degree levels. Level 1 indicates low purifying power, and level 3 indicates high purifying power. Level 2 corresponds to intermediate purifying power between level 1 and level 3.

In the example illustrated in FIG. 5, the numbers of shoots "large", "medium", and "small", concentrations "high", "medium", and "low", and gas volumes "large", "medium", and "small" are assigned to levels 1, 2, and 3, respectively. Levels 1 to 3 differ from each other in the number of shoots, the concentration, and the gas volume. The assignment described above is merely one example.

The number of shoots corresponds to the number of vortex rings 148 that are shot in response to a single purification instruction. As the number of shoots increases, a larger number of vortex rings 148 are shot, and a larger amount of the chemical agent reaches a target position, thus making it possible to purify the target position with a higher intensity.

The concentration of the chemical agent is the concentration of the chemical agent contained in one vortex ring 148. As the concentration increases, the amount of the chemical agent contained in the vortex ring 148 increases, and a larger amount of the chemical agent reaches a target position, thus making it possible to purify the target position with a higher intensity.

The gas volume corresponds to the size of one vortex ring 148. As the gas volume increases, the size of the vortex ring 148 increases. Since the size of the vortex ring 148 increases in front-and-rear directions, the time for which the vortex ring 148 contacts the target position increases. Thus, a large amount of the chemical agent contacts the target position, thus making it possible to purify the target position with a high intensity.

When the contamination-degree level is "30" or more, an emergency operation is associated therewith as the shooting control information. The contamination-degree level "30" corresponds to the second threshold. For the emergency operation, "maximum" is allocated to all of the number of shoots, the concentration, and the gas volume. That is, the vortex ring 148 is shot with the maximum output power in the range of power that can be output by the purifying unit 140. The shooting control parameters for the emergency operation may be the same as the shooting control parameters for level 3.

The shooting control parameters may include at least one of the number of shoots of the vortex ring 148, the concentration of the chemical agent contained in the vortex ring 148, and the gas volume of the vortex ring 148. For example, the shooting control parameters may include only the number of shoots of the vortex ring 148. That is, it is sufficient that the purifying device 102 be able to change at least one of the number of shoots, the concentration of the chemical agent, and the gas volume, and any of the number of shoots, the concentration of the chemical agent, and the gas volume may be a fixed value.

Although an example in which the contamination-degree levels are divided into the ranges of five stages is illustrated in FIG. 5, the division of the contamination-degree levels is not limited thereto. For example, the ranges of the contamination-degree levels may be two stages, three stages, four stages, or six stages or more. Also, at least one of the suspension of the shooting and the emergency operation does not necessarily have to be associated as the shooting control information.

The correspondence information 134 illustrated in FIG. 5 may be updatable. For example, the correspondence information 134 may be updated based on the type of chemical agent stored in a liquid reservoir 142 in the purifying unit 140, the strength of the purifying power, or the like. For example, when the chemical agent stored in the liquid reservoir 142 has a strong purifying power, the amount of the chemical agent to be used can be reduced. Thus, when the chemical agent has a strong purifying power, the number of shoots, the concentration, and the gas volume may be updated to have smaller values. Alternatively, pieces of correspondence information 134 may be stored in the storage 130 for respective types of chemical agent or respective strengths of the purifying power.

The purifying unit 140 is one example of a discharger that has a container for storing a chemical agent and that discharges the chemical agent stored in the container. For example, the purifying unit 140 shoots the chemical agent to a target position in a localized manner. Specifically, when the controller 120 obtains the purification instruction, the purifying unit 140 shoots the chemical agent. In the present embodiment, the purifying unit 140 shoots the vortex ring 148, which is formed of gas containing the chemical agent, to a target position.

As illustrated in FIG. 1, the purifying unit 140 includes the liquid reservoir 142, a hollow portion 144, and the shooting port 146. The liquid reservoir 142 is one example of a container for storing the chemical agent. The hollow portion 144 is a space in which the gas for forming the vortex ring 148 is stored. The shooting port 146 is an aperture that connects the hollow portion 144 to the outside and from which the vortex ring 148 is shot.

The hollow portion 144 has, for example, a structure (not illustrated) for instantaneously changing its internal capacity in order to eject the gas stored therein. For example, the hollow portion 144 has therein an elastic membrane member and a hitting device for changing the membrane member by hitting it.

The hitting device instantaneously deforms the membrane member to thereby cause the gas to be ejected from the shooting port 146. The vortex ring 148 is formed when the gas ejected from the hollow portion 144 passes through the shooting port 146 and is shot in a predetermined direction.

The orientation of the shooting port 146 can be changed, for example, in up-and-down directions and left-and-right directions. This allows the purifying unit 140 to shoot the vortex ring 148 to a plurality of target positions.

The input unit 160 receives an operation input externally performed on the purifying device 102. The input unit 160 is implemented by, for example, a touch panel display, a physical button switch, or the like. Alternatively, the input unit 160 may be implemented by a receiver that receives an operation input from a remote operation terminal (a remote controller) for the purifying device 102. For example, a button switch for executing the purifying may be provided on an outer casing of the purifying device 102 as the input unit 160. When the button switch is pressed, the instruction generator 124 may generate the purification instruction.

The input unit 160 may also receive an input of the schedule information. Alternatively, the input unit 160 may receive an update instruction and specific update details for the correspondence information 134.

[Operation]

Subsequently, the operation of the purifying system 100 according to the present embodiment, that is, a purifying method according to the present embodiment, will be described with reference to FIGS. 6 and 7.

Figure 6:
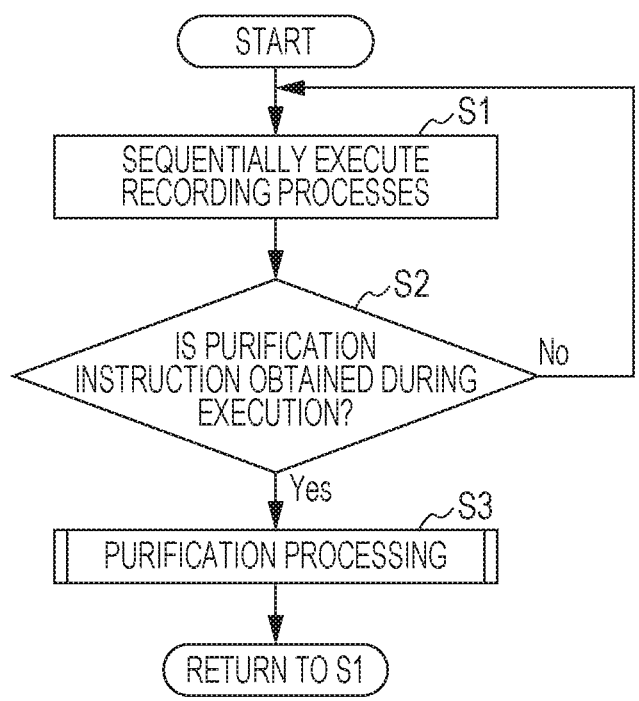
FIG. 6 is a flowchart illustrating the operation of the purifying system according to the first embodiment.

FIG. 6 is a flowchart illustrating the operation of the purifying system 100 according to the present embodiment. FIG. 7 is a flowchart illustrating recording processes included in the operation of the purifying system 100 according to the present embodiment.

As illustrated in FIG. 6, first, the purifying system 100 sequentially executes recording processes (S1). The recording processes are sequentially executed at arbitrary time intervals. That is, the recording processes may be sequentially executed at regular time intervals or may be sequentially executed at random time intervals.

Figure 7:
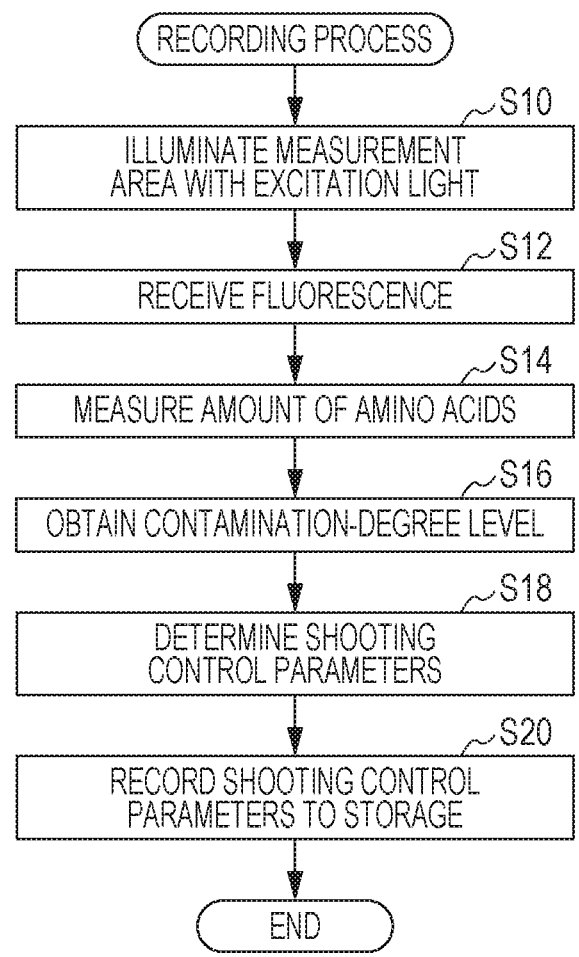
FIG. 7 is a flowchart illustrating recording processes included in the operation of the purifying system according to the first embodiment.

Specifically, as illustrated in FIG. 7, first, the light source 112a in the contamination sensor 112 illuminates a measurement area with excitation light (S10). Next, the light-receiving element 112b in the contamination sensor 112 receives fluorescence that returns from the measurement area (S12). The light-receiving element 112b performs photoelectric conversion to generate an electrical signal corresponding to the intensity of the fluorescence and outputs the generated electrical signal to the signal processing circuit 112d.

Next, based on the intensity of the fluorescence, the signal processing circuit 112d measures the amount of amino acids in the measurement area (S14). Specifically, the signal processing circuit 112d calculates the amount of amino acids by processing the electrical signal output from the light-receiving element 112b. Next, the signal processing circuit 112d obtains a contamination-degree level (S16). For example, the signal processing circuit 112d determines a contamination-degree level, based on the calculated amount of amino acids. The contamination sensor 112 outputs the determined contamination-degree level to the purifying device 102.

Next, based on the contamination-degree level obtained from the contamination sensor 112 via the communication unit 110, the sensor controller 122 in the purifying device 102 determines shooting control parameters for the chemical agent (S18). Specifically, by referring to the correspondence information 134 stored in the storage 130, the sensor controller 122 determines the shooting control parameters corresponding to the contamination-degree level. Lastly, the sensor controller 122 records the determined shooting control parameters to the storage 130 (S20).

When the recording process illustrated in FIG. 7 is sequentially executed, the shooting control information indicating the shooting control parameters is sequentially recorded, for example, as illustrated in FIG. 4. The storage 130 does not necessarily have to store therein a plurality of pieces of shooting control information and may store therein only one piece of shooting control information recorded in the most-recent recording process. That is, in each recording process, update processing may be performed to delete old shooting control information and record new shooting control information.

Referring back to FIG. 6, when a purification instruction is obtained during execution of the recording processes (Yes in S2), the purifying system 100 performs purification processing (S3). If no purification instruction is obtained (No in S2), the recording process illustrated in FIG. 7 is performed again.

Figure 8:
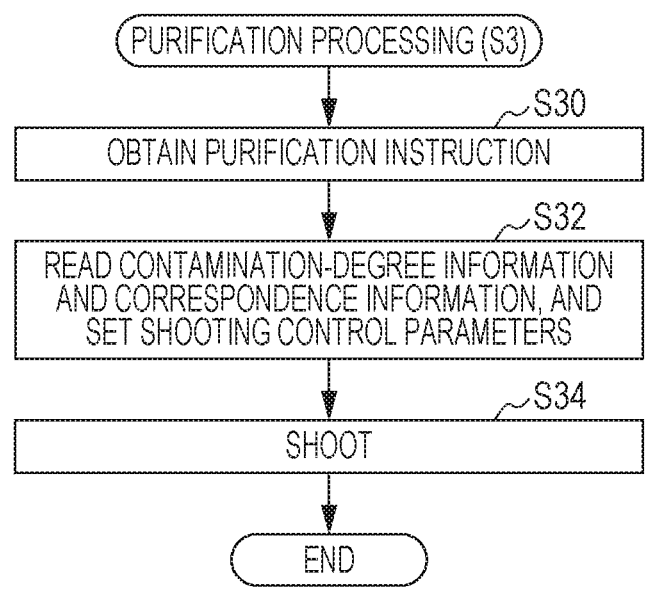
FIG. 8 is a flowchart illustrating the operation of the purifying device according to the first embodiment, the operation being performed when a purification instruction is obtained.

FIG. 8 is a flowchart illustrating an operation of the purifying system 100 according to the present embodiment, the operation being performed when the purification instruction is obtained.

Next, the operation of the purifying device 102 when the purification instruction is obtained will be described with reference to FIG. 8. That is, a description will be given of a specific example of the purification processing (S3) illustrated in FIG. 6.

FIG. 8 is a flowchart illustrating an operation of the purifying device 102 according to the present embodiment, the operation being performed when the purification instruction is obtained. The operation illustrated in FIG. 8 is mainly executed by the purification controller 126.

First, the purification controller 126 obtains the purification instruction (S30). The purification instruction is generated by the instruction generator 124 at a timing based on the schedule information or at a timing at which an input from the outside is received.

The purification controller 126 reads the contamination-degree information 132 and the correspondence information 134 from the storage 130 and sets shooting control parameters corresponding to the contamination-degree level (S32). Specifically, the purification controller 126 sets, as the shooting control parameters, the number of shoots, the concentration, and the gas volume in the shooting control information associated with a time point that is the closest to the time point at which the purification instruction was obtained.

Based on the conditions of the set number of shoots, concentration, and gas volume, the purification controller 126 controls the purifying unit 140 to shoot the vortex ring 148 (S34).

In the purifying system 100 and the purifying device 102 according to the present embodiment, the shooting control parameters for the vortex ring 148 are determined based on the detected contamination-degree level of the target position, as described above. Thus, the amount of the chemical agent contained in the vortex ring 148 can be adjusted to an appropriate amount. This allows the purifying system 100 and the purifying device 102 to efficiently purify the target position.

[Modification]

Now, the operation of the purifying system 100 when the detected contamination-degree level exceeds the second threshold described above, and the purification is emergently needed will be described with reference to FIG. 9 as a modification of the present embodiment.

Figure 9:
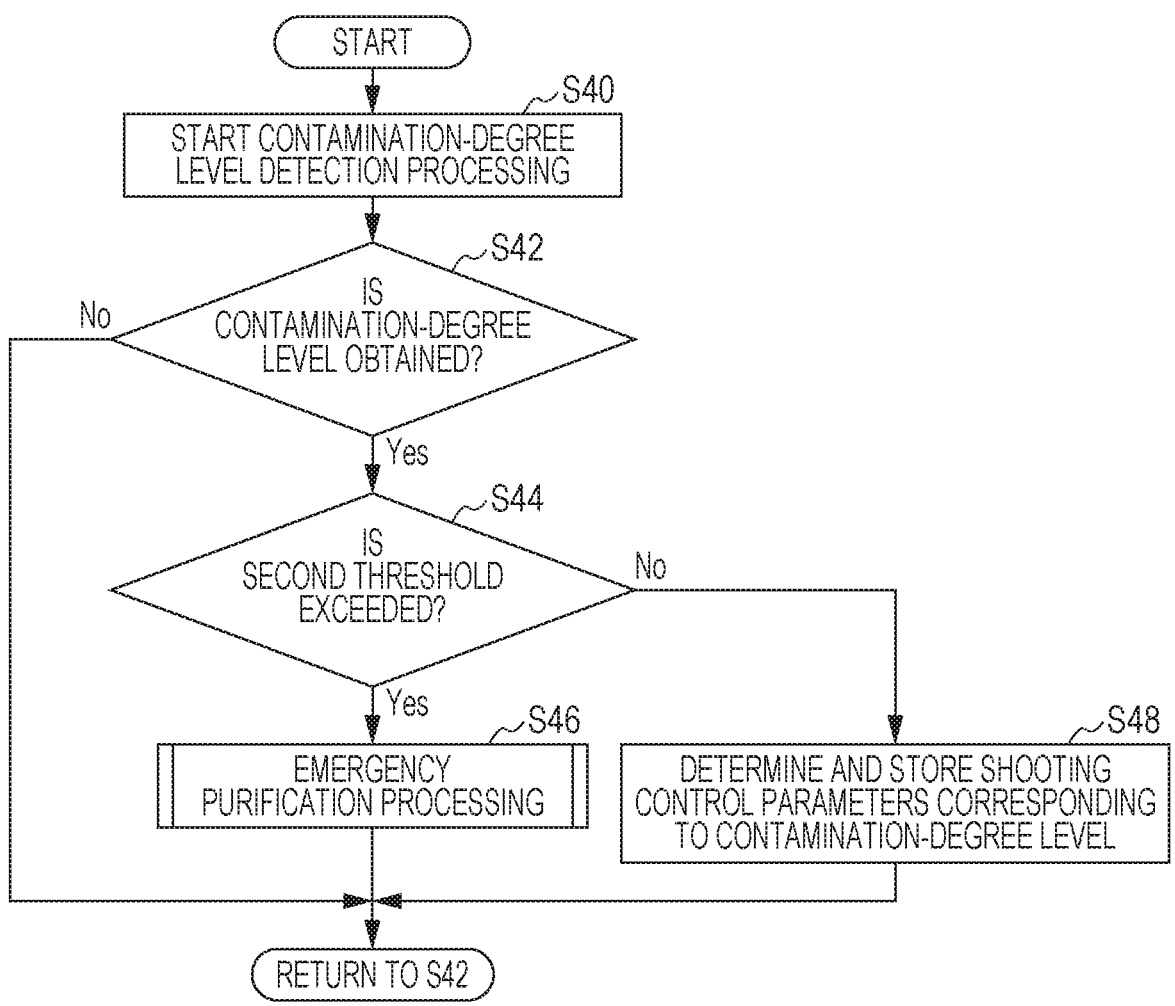
FIG. 9 is a flowchart illustrating a modification of the recording processes included in the operation of the purifying device according to the first embodiment.

FIG. 9 is a flowchart illustrating a modification of the recording processes included in the operation of the purifying device 102 according to the present embodiment. The operation illustrated in FIG. 9 is mainly executed by the sensor controller 122.

First, the sensor controller 122 causes the contamination sensor 112 to start contamination-degree level detection processing (S40). After starting the detection processing, for example, the contamination sensor 112 periodically and repeatedly detects the contamination-degree level of the target position. Alternatively, the contamination sensor 112 may detect the contamination-degree level at a timing indicated by an instruction from the sensor controller 122. Specifically, as illustrated in FIG. 7, the contamination sensor 112 executes the excitation light illumination (S10) to the contamination-degree level obtaining (S16).

The sensor controller 122 stands by until obtaining the contamination-degree level from the contamination sensor 112 (No in S42). Specifically, the sensor controller 122 stands by until obtaining the contamination-degree level from the contamination sensor 112 via the communication unit 110.

Upon obtaining the contamination-degree level (Yes in S42), the sensor controller 122 compares the obtained contamination-degree level with the second threshold (S44). If the contamination-degree level exceeds the second threshold (Yes in S44), the sensor controller 122 generates an emergency purification instruction and causes the purification controller 126 to perform emergency purification processing (S46). A specific operation of the emergency purification processing is described later with reference to FIG. 10.

If the contamination-degree level does not exceed the second threshold (No in S44), the sensor controller 122 determines shooting control parameters corresponding to the contamination-degree level and stores the shooting control parameters in the storage 130 (S48). Specifically, by referring to the correspondence information 134 on the basis of the obtained contamination-degree level, the sensor controller 122 determines the shooting control information, specifically, the shooting control parameters, corresponding to the range to which the obtained contamination-degree level belongs. The sensor controller 122 stores the determined shooting control information, together with the contamination-degree level, in the storage 130 in association with the detection time point.

Subsequently, each time the contamination-degree level is obtained (Yes in S42) the processing from steps S44 to S48 is repeated. As a result, the contamination-degree information 132 in which the contamination-degree levels and pieces of shooting control information are associated with detection time points, respectively, is stored in the storage 130, as illustrated in FIG. 4.

Figure 10:
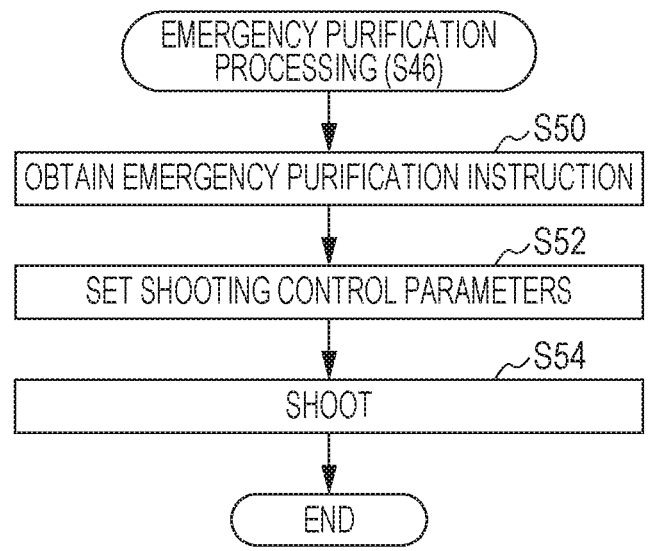
FIG. 10 is a flowchart illustrating the operation of the purifying device according to the first embodiment, the operation being performed when an emergency purification instruction is obtained.

FIG. 10 is a flowchart illustrating an operation of the purifying device 102 according to the present embodiment, the operation being performed when the emergency purification instruction is obtained. The operation illustrated in FIG. 10 is mainly executed by the purification controller 126.

First, the purification controller 126 obtains an emergency purification instruction (S50). As illustrated in FIG. 9, the emergency purification instruction is generated when the contamination-degree level obtained by the contamination sensor 112 exceeds the second threshold. Specifically, the emergency purification instruction is generated when the contamination-degree level is high, and the degree of emergency in high in that disease infection is highly likely to spread.

The purification controller 126 sets the shooting control parameters determined based on the contamination-degree level (S52). In this case, since the contamination-degree level exceeds the second threshold to reach a sufficiently large value, the shooting control parameters correspond to the shooting control parameters for emergency. Specifically, the purification controller 126 sets the number of shoots, the concentration, and the gas volume to "maximum", as indicated by the correspondence information 134.

The purification controller 126 controls the purifying unit 140, based on the conditions of the set number of shoots, concentration, and gas volume, to shoot the vortex ring 148 (S54).

This makes it possible to purify the target position without waiting for the normal purification instruction. Accordingly, it is possible to prevent or reduce disease spread due to contamination.

Second Embodiment

A second embodiment will be described next.

The description in the first embodiment has been given of an example in which the shooting control parameters are determined based on the contamination-degree level, and the purification is performed based on the determined shooting control parameters. In contrast, in the second embodiment, a description will be given of an example in which the purification is performed based on a measured amount of amino acids without determining the shooting control parameters. Points that differ from the first embodiment are mainly described below, and points that are common to both the embodiments are not described or are briefly described.

[Configuration]

First, the configuration of a purifying system 200 according to the present embodiment will be described with reference to FIG. 11.

Figure 11:
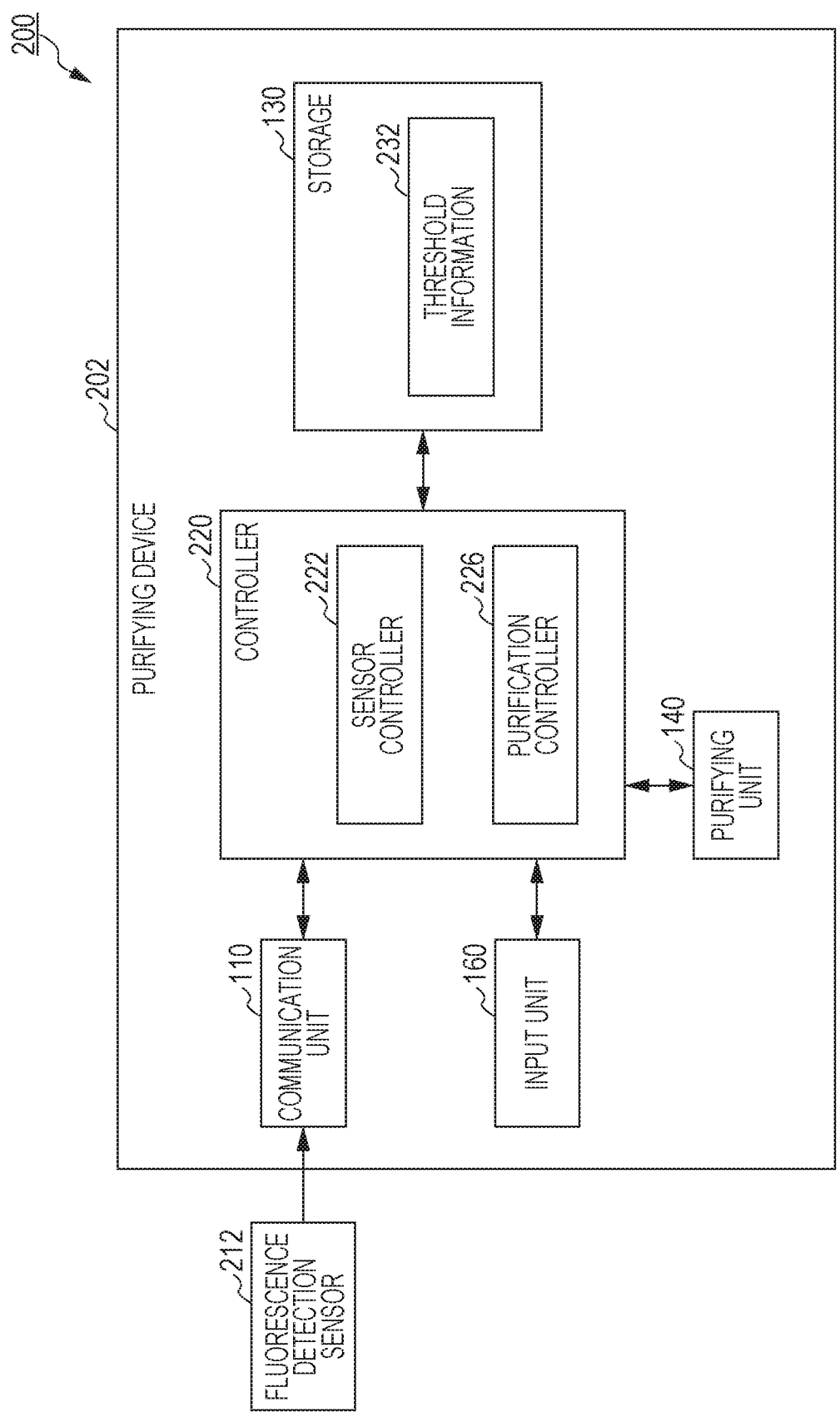
FIG. 11 is a block diagram illustrating the configuration of a purifying system according to a second embodiment.

FIG. 11 is a block diagram illustrating the configuration of the purifying system 200 according to the present embodiment. As illustrated in FIG. 11, the purifying system 200 includes a purifying device 202 and a fluorescence detection sensor 212.

The fluorescence detection sensor 212 illuminates a measurement area with excitation light, detects fluorescence from the measurement area, and measures the amount of amino acids contained in the measurement area, based on the intensity of the detected fluorescence. Specifically, the fluorescence detection sensor 212 has a configuration that is substantially the same as the configuration of the contamination sensor 112 according to the first embodiment and outputs a measurement value of the amount of amino acids instead of the contamination-degree level. More specifically, the fluorescence detection sensor 212 includes a light source 112a, a light-receiving element 112b, a spectroscopic element 112c, and a signal processing circuit 112d that are substantially the same as those in the contamination sensor 112 illustrated in FIG. 3. In this case, the signal processing circuit 112d outputs a measurement value of the amount of amino acids.

Compared with the purifying device 102 according to the first embodiment, the purifying device 202 differs in that it includes a controller 220 in place of the controller 120, and threshold information 232, instead of the contamination-degree information 132 and the correspondence information 134, is stored in a storage 130, as illustrated in FIG. 11. In the present embodiment, a communication unit 110 communicates with the fluorescence detection sensor 212 instead of the contamination sensor 112.

As illustrated in FIG. 11, the controller 220 includes a sensor controller 222 and a purification controller 226. The controller 220 is implemented by, for example, a nonvolatile memory in which a program is stored, a volatile memory that is a temporary storage area for executing the program, input/output ports, and a processor that executes the program. Each of the sensor controller 222 and the purification controller 226 included in the controller 220 may be implemented by software executed by a processor or may be implemented by hardware, such as an electronic circuit including a plurality of circuit elements.

The sensor controller 222 controls operations related to the fluorescence detection sensor 212. Specifically, the sensor controller 222 obtains a measurement value of the amount of amino acids, the measurement value being output from the fluorescence detection sensor 212 via the communication unit 110, and compares the obtained measurement value with a first threshold. The first threshold is a value indicated by the threshold information 232 stored in the storage 130. The first threshold is, for example, a predetermined value for determining whether or not the purification is to be performed. The first threshold may be, for example, 0. In this case, the sensor controller 222 can determine whether or not amino acids are present in the measurement area. The sensor controller 222 outputs a result of the comparison to the purification controller 226.

Based on the result of the comparison, the purification controller 226 controls the purifying unit 140. Specifically, when the amount of amino acids exceeds the first threshold, the purification controller 226 causes the purifying unit 140 to discharge the chemical agent to the measurement area. When the amount of amino acids is smaller than or equal to the first threshold, the purification controller 226 suspends the sanitizing-agent discharge performed by the purifying unit 140. For example, when the first threshold is 0, the chemical agent is discharged when amino acids that make up germs or viruses are present. Thus, the chemical agent breaks down the germs or viruses to make it possible to purify the measurement area.

In the present embodiment, the purification controller 226 uses predetermined shooting control parameters. Thus, regardless of whether the amount of amino acids is large or small, the purifying unit 140 shoots the vortex ring 148 in accordance with a predetermined number of shoots, concentration of the chemical agent, and gas volume.

[Operation]

Figure 12:
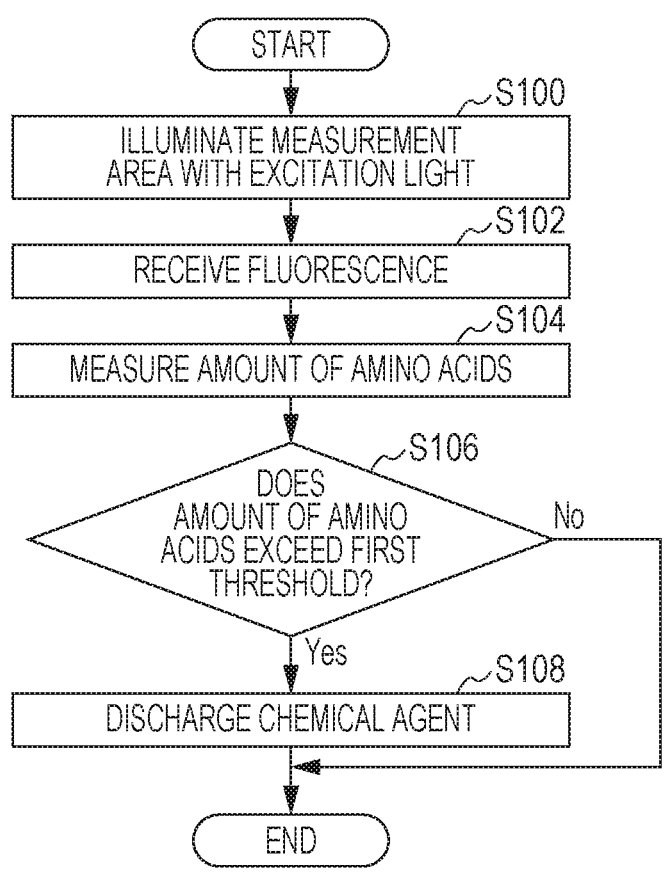
FIG. 12 is a flowchart illustrating the operation of the purifying system according to the second embodiment.

Next, the operation of the purifying system 200 according to the present embodiment will be described with reference to FIG. 12. FIG. 12 is a flowchart illustrating the operation of the purifying system 200 according to the present embodiment.

As illustrated in FIG. 12, first, the fluorescence detection sensor 212 illuminates a measurement area with excitation light (S100). Next, the fluorescence detection sensor 212 receives fluorescence that returns from the measurement area (S102). The fluorescence detection sensor 212 performs photoelectric conversion to generate an electrical signal corresponding to the intensity of the fluorescence and measures the amount of amino acids, based on the generated electrical signal (S104). The fluorescence detection sensor 212 outputs a measurement value of the amount of amino acids to the purifying device 202. In the purifying device 202, the sensor controller 222 in the controller 220 obtains the measurement value of the amount of amino acids via the communication unit 110.

Next, the sensor controller 222 compares the obtained measurement value of the amount of amino acids with the first threshold indicated by the threshold information 232 stored in the storage 130 (S106). If the amount of amino acids exceeds the first threshold (Yes in S106), the sensor controller 222 causes the purifying unit 140 to discharge the chemical agent (S108). If the amount of amino acids is smaller than or equal to the first threshold (No in S106), the chemical agent is not discharged, and the processing ends.

In the present embodiment, the excitation light illumination is performed when an instruction from a user is received. Alternatively, the excitation light illumination is performed based on predetermined schedule information.

The chemical agent is discharged when the amount of amino acids exceeds the first threshold, as described above, and thus, when germs or viruses are present, amino acids that make up the germs or viruses are detected, and thus the purification is performed. When the amount of amino acids is smaller than or equal to the first threshold, that is, no germs or viruses are present, the chemical agent is not discharged, thus making it possible to reduce unwanted use of the chemical agent.

[Modification]

Now, a modification of the present embodiment will be described. In this modification, a contamination-degree level is determined, shooting control parameters are determined based on the determined contamination-degree level, and the purification is performed using the determined shooting control parameters, as in the first embodiment.

Figure 13:
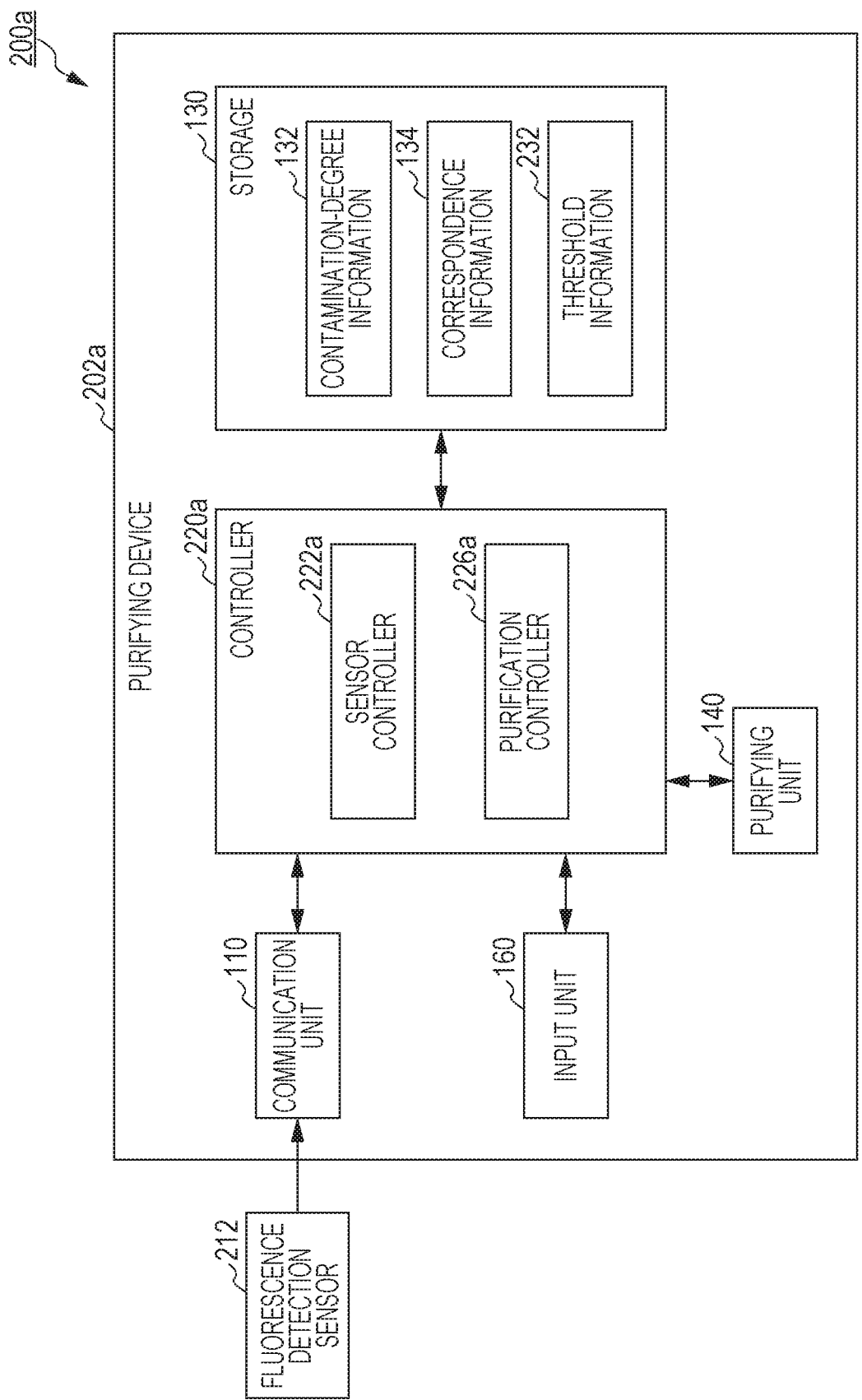
FIG. 13 is a block diagram illustrating the configuration of a purifying system according to a modification of the second embodiment.

FIG. 13 is a block diagram illustrating the configuration of a purifying system 200a according to this modification. As illustrated in FIG. 13, the purifying system 200a includes a purifying device 202a and a fluorescence detection sensor 212.

The fluorescence detection sensor 212 outputs a measurement value of the amount of amino acids, as in the second embodiment. Although an example in which the purifying device 202a determines the contamination-degree level is described in this modification, the purifying system 200a may include the contamination sensor 112 in place of the fluorescence detection sensor 212, and the contamination sensor 112 may determine the contamination-degree level, as in the first embodiment.

Compared with the purifying device 202 according to the second embodiment, the purifying device 202a includes a controller 220a in place of the controller 220, as illustrated in FIG. 13. The storage 130 stores, therein, not only the threshold information 232 but also the contamination-degree information 132 and the correspondence information 134. The contamination-degree information 132 and the correspondence information 134 are substantially the same as those in the first embodiment.

As illustrated in FIG. 13, the controller 220a includes a sensor controller 222a and a purification controller 226a. The controller 220a is implemented by, for example, a nonvolatile memory in which a program is stored, a volatile memory that is a temporary storage area for executing the program, input/output ports, and a processor that executes the program. Each of the sensor controller 222a and the purification controller 226a included in the controller 220 may be implemented by software executed by a processor or may be implemented by hardware, such as an electronic circuit including a plurality of circuit elements.

The sensor controller 222a performs a combined operation of the operation of the sensor controller 122 in the first embodiment and the operation of the sensor controller 222 in the second embodiment. Similarly, the purification controller 226a performs a combined operation of the operation of the purification controller 126 in the first embodiment and the operation of the purification controller 226 in the second embodiment. A specific example of these operations will be described below with reference to the flowchart illustrated in FIG. 14.

Figure 14:
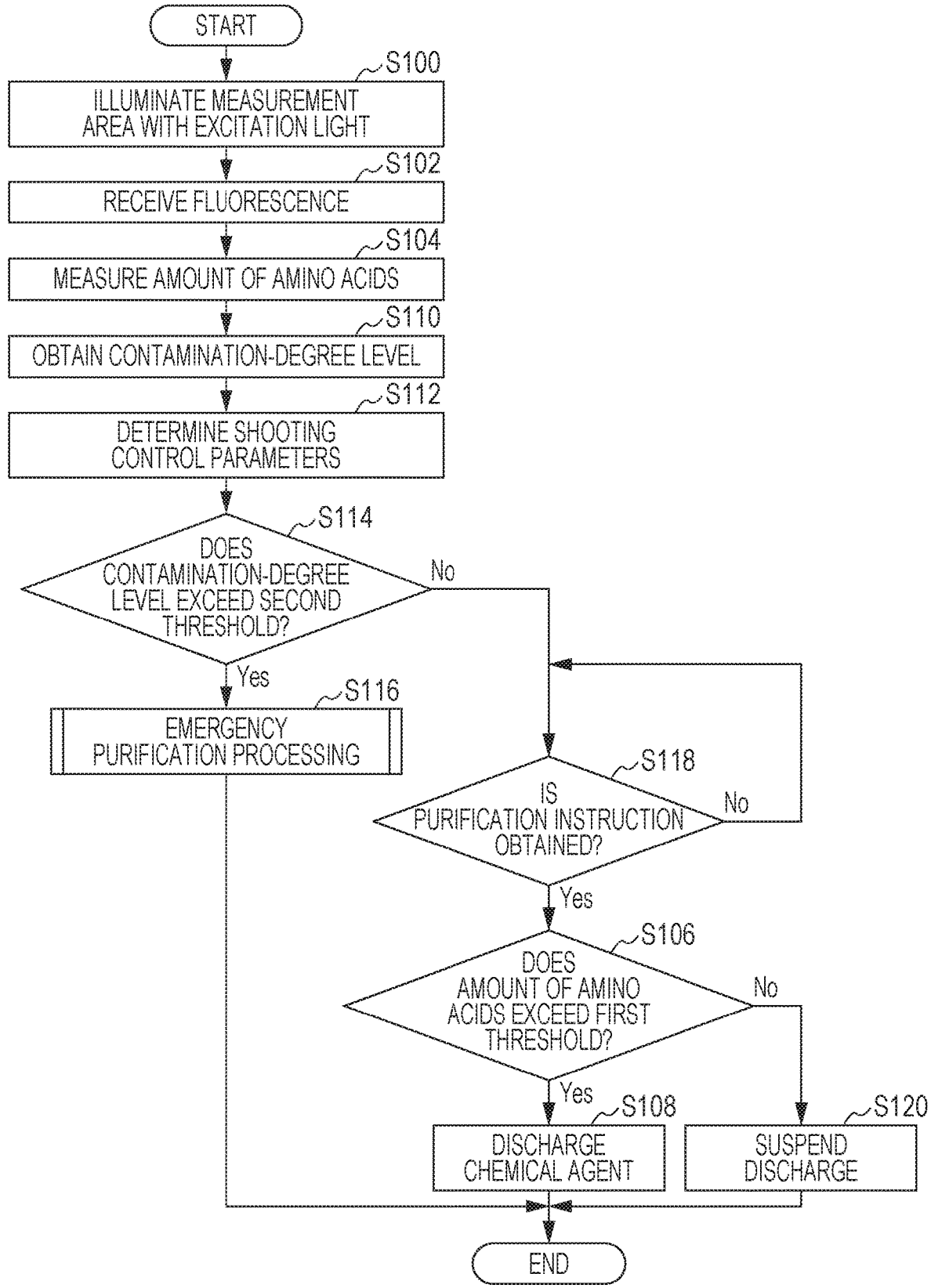
FIG. 14 is a flowchart illustrating the operation of the purifying system according to the modification of the second embodiment.

FIG. 14 is a flowchart illustrating the operation of the purifying system 200a according to this modification.

As illustrated in FIG. 14, processing from the excitation light illumination performed by the fluorescence detection sensor 212 (S100) to the measurement of the amount of amino acids (S104) is substantially the same as the processing in the second embodiment.

Next, based on the amount of amino acids obtained from the fluorescence detection sensor 212, the sensor controller 222a obtains the contamination-degree level (S110). Specifically, based on the amount of amino acids which is calculated based on the intensity of the fluorescence, the sensor controller 222a determines the contamination-degree level. Next, by referring to the correspondence information 134 stored in the storage 130, the sensor controller 222a determines the shooting control parameters, based on the determined contamination-degree level (S112).

Subsequently, the sensor controller 222a compares the contamination-degree level with the second threshold (S114). If the contamination-degree level exceeds the second threshold (Yes in S114), the sensor controller 222a generates an emergency purification instruction to cause the purification controller 226a to perform emergency purification processing (S116). The emergency purification processing (S116) is substantially the same as the processing illustrated in FIG. 10.

If the contamination-degree level is lower than or equal to the second threshold (No in S114), the purification controller 226a stands by until obtaining a purification instruction (No in S118). Upon obtaining the purification instruction (Yes in S118), the purification controller 226a compares the amount of amino acids measured in step S104 with the first threshold (S106). If the amount of amino acids exceeds the first threshold (Yes in S106), the sensor controller 222 causes the purifying unit 140 to discharge the chemical agent (S108). If the amount of amino acids is smaller than or equal to the first threshold (No in S106), the purification controller 226a suspends the discharge of the chemical agent (S120).

As described above, when the contamination-degree level exceeds the second threshold, it is possible to purify the measurement area without waiting for obtaining the purification instruction. Also, even when the purification instruction is obtained, the discharge of the chemical agent is suspended when the amount of amino acids is smaller than or equal to the first threshold, that is, when germs or viruses are not present. This makes it possible to reduce unwanted use of the chemical agent.

Third Embodiment

A third embodiment will be described next.

The description in the second embodiment has been given of an example in which the measurement of the amount of amino acids is started based on an instruction from a user or based on predetermined schedule information. In contrast, in the third embodiment, the start of the measurement of the amount of amino acids is determined based on a human operation. Points that differ from the first or second embodiment are mainly described below, and points that are the same as those in the above-described embodiments are not described or are briefly described.

[Configuration]

First, the configuration of a purifying system 300 according to the present embodiment will be described with reference to FIG. 15.

Figure 15:
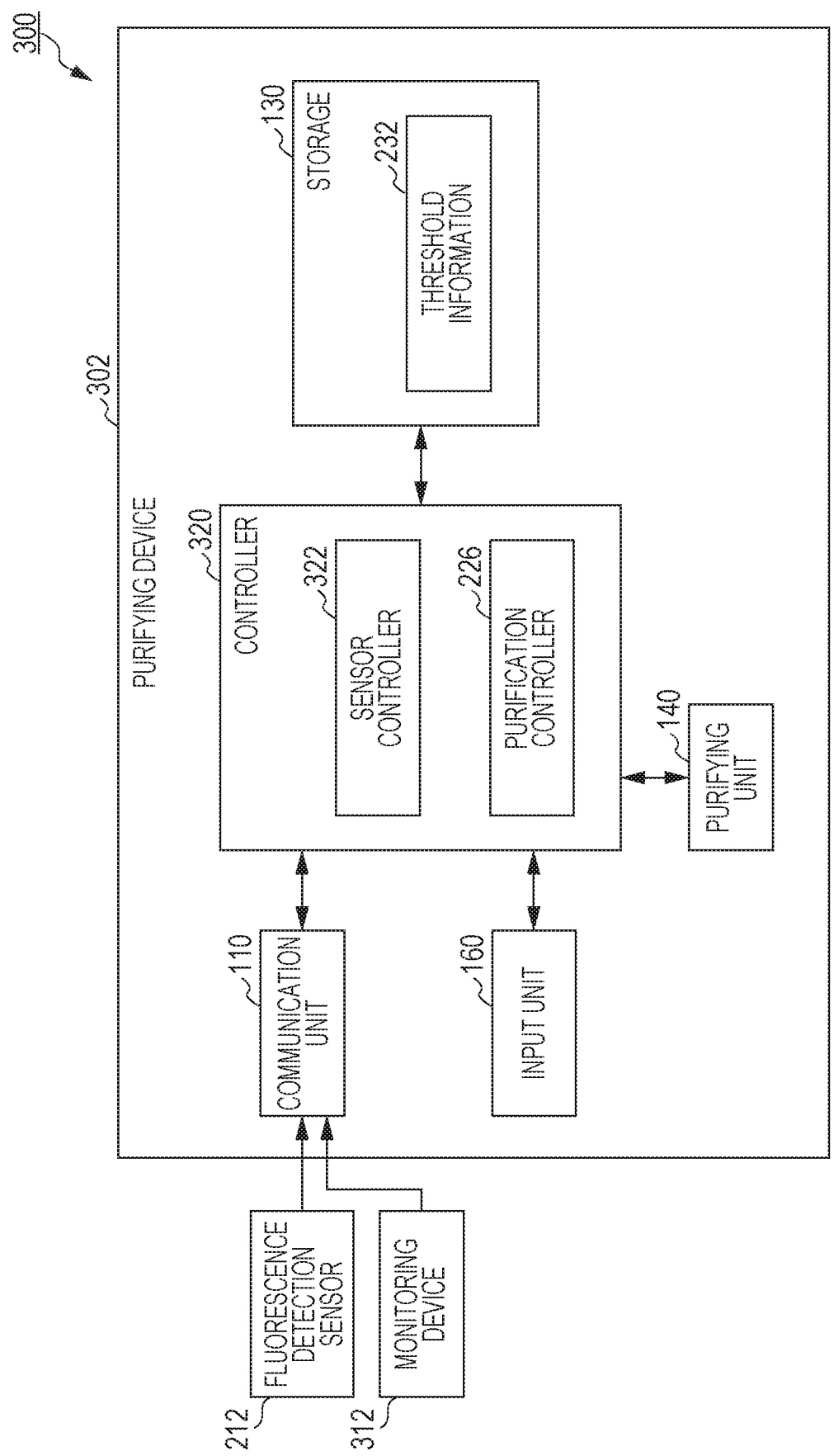
FIG. 15 is a block diagram illustrating the configuration of a purifying system according to a third embodiment.

FIG. 15 is a block diagram illustrating the configuration of the purifying system 300 according to the present embodiment. As illustrated in FIG. 15, the purifying system 300 includes a purifying device 302, a fluorescence detection sensor 212, and a monitoring device 312.

The monitoring device 312 monitors a user's operation. Specifically, the monitoring device 312 monitors a user's contact operation on an object included in a measurement area. The monitoring device 312 is, for example, a surveillance camera, or may be a contact sensor. The object included in the measurement area may be, for example, part of the walls, the ceiling, and the floor that define the space 90 or may be household electrical or electronic equipment, an operation terminal, or the like that is present in the space 90. For example, when the object included in the measurement area is the doorknob 94, the monitoring device 312 may be a camera that photographs a range including the doorknob 94 or a contact sensor attached to the doorknob 94.

The monitoring device 312 determines whether or not a user's contact operation on the object included in measurement area is performed and outputs a result of the determination to the purifying device 302. Alternatively, the monitoring device 312 may output information for determining whether or not a contact operation has been performed to the purifying device 302. The information may include, for example, video data resulting from photography of the object included in the measurement area. In this case, based on the information output from the monitoring device 312, the purifying device 302 determines whether or not a user's contact operation has been performed.

The purifying device 302 differs from the purifying device 202 according to the second embodiment in that a controller 320 is provided in place of the controller 220, as illustrated in FIG. 15. Compared with the controller 220, the controller 320 includes a sensor controller 322 in place of the sensor controller 222.

The controller 320 is implemented by, for example, a nonvolatile memory in which a program is stored, a volatile memory that is a temporary storage area for executing the program, input/output ports, and a processor that executes the program. Each of the sensor controller 322 and the purification controller 226 included in the controller 320 may be implemented by software executed by a processor or may be implemented by hardware, such as an electronic circuit including a plurality of circuit elements.

The sensor controller 322 controls operations related to the fluorescence detection sensor 212. Specifically, the sensor controller 322 controls the timing at which the fluorescence detection sensor 212 measures the amount of amino acids, in addition to the operation performed by the sensor controller 222. More specifically, based on a determination result output from the monitoring device 312, the sensor controller 322 determines whether or not a user's contact operation on the object included in the measurement area is finished. After the contact operation is finished, the sensor controller 322 causes the fluorescence detection sensor 212 to measure the amount of amino acids. For example, the sensor controller 322 generates a start signal for starting the measurement operation and outputs the generated start signal to the fluorescence detection sensor 212 via the communication unit 110. Upon receiving the start signal, the fluorescence detection sensor 212 illuminates the measurement area with excitation light.

[Operation]

Next, the operation of the purifying system 300 according to the present embodiment will be described with reference to FIG. 16.

Figure 16:
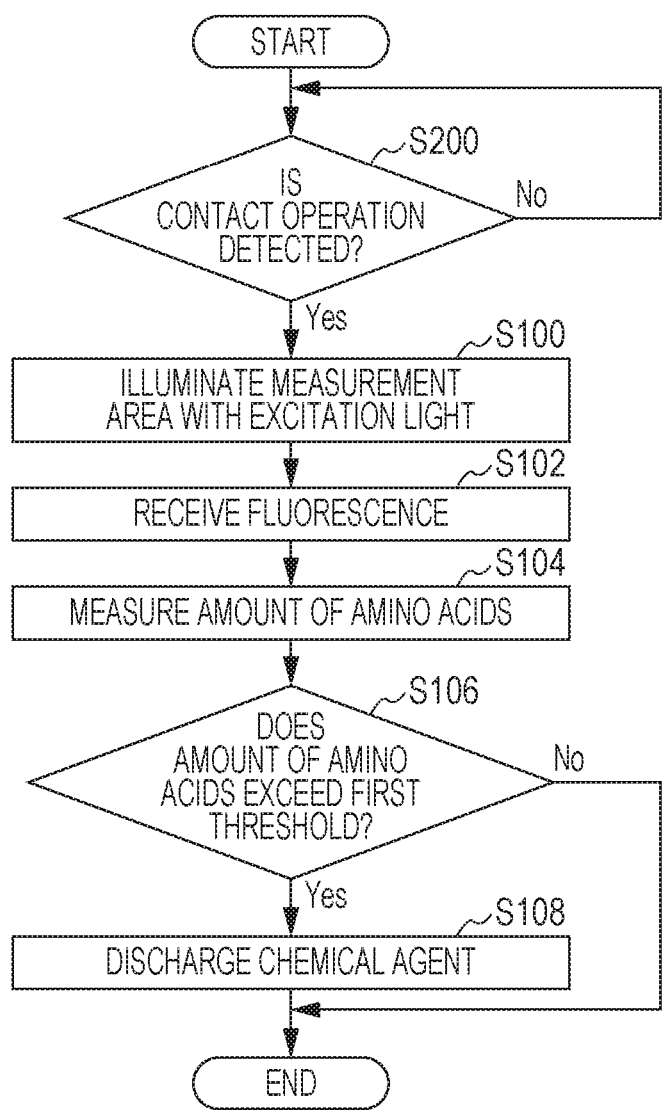
FIG. 16 is a flowchart illustrating the operation of the purifying system according to the third embodiment.

FIG. 16 is a flowchart illustrating the operation of the purifying system 300 according to the present embodiment. As illustrated in FIG. 16, the fluorescence detection sensor 212 and the purifying device 302 are in a standby state until a contact operation on an object included in a measurement area is performed (No in S200). If the monitoring device 312 detects a contact operation on the object included in the measurement area (Yes in S200), the fluorescence detection sensor 212 illuminates the measurement area with excitation light (S100). The subsequent processing is substantially the same as the processing in the second embodiment.

When a contact operation is performed, there is a possibility that germs or viruses adhere to the object touched by the user. Thus, when a contact operation is performed, the fluorescence detection sensor 212 is caused to measure the amount of amino acids, thereby making it possible to perform the purifying before another person contacts the object. Therefore, according to the present embodiment, it is possible to prevent or reduce disease spread due to contact infection.

Also, contact infection does not spread unless the user does not touch the object. Thus, the number of times or the frequency at which the amount of amino acids is measured can be reduced, thus making it possible to reduce power consumed by the fluorescence detection sensor 212. As described above, the purifying system 300 according to the present embodiment makes it possible to efficiently purify a measurement area while reducing power that is consumed.

The fluorescence detection sensor 212 may sequentially measure the amount of amino acids at arbitrary time intervals, as in the contamination sensor 112 according to the first embodiment. For example, the fluorescence detection sensor 212 repeatedly measures the amount of amino acids at predetermined time intervals. In this case, the fluorescence detection sensor 212 additionally measures the amount of amino acids when the start signal is received.

The purifying system 300 according to the present embodiment may also include the contamination sensor 112 in place of the fluorescence detection sensor 212. The contamination sensor 112 may measure the amount of amino acid and determine the contamination-degree level after the contact operation is finished.

Other Embodiments

Although the purifying device, the purifying system, and the purifying method according to one or more aspects have been described above in conjunction with the embodiments, the present disclosure is not limited to the embodiments. A mode obtained by making various variations conceived by those skilled in the art to the embodiments and a mode constructed by a combination of some of the constituent elements in different embodiments are also encompassed by the scope of the present disclosure, as long as such modes do not depart from the spirit of the present disclosure.

For example, although, in the embodiments described above, the purifying device 102 shoots the chemical agent by shooting the vortex ring 148 containing the chemical agent, the sanitizing-agent shooting method does not necessarily have to utilize the vortex ring 148. For example, the purifying device 102 may have a nozzle from which the chemical agent is sprayed in a mist or gas form. Alternatively, the purifying device 102 may transport a microparticulated chemical agent by employing a transportation technique using ultrasonic waves.

Also, for example, although an example in which the contamination-degree level detected by the contamination sensor 112 and the shooting control parameters (specifically, the shooting control information) determined based on the contamination-degree level are stored has been described in the above embodiments, either the contamination-degree level or the shooting control parameters do not necessarily have to be stored in the storage 130. Specifically, the contamination-degree information 132 may indicate only the contamination-degree levels associated with the detection time points or may indicate only the shooting control parameters associated with the detection time points.

For example, when only the contamination-degree levels are stored in the storage 130, upon obtaining the purification instruction, the purification controller 126 determines the shooting control parameters, based on the contamination degree associated with the most-recent detection time point, and controls the purifying unit 140, based on the determined shooting control parameters.

Also, for example, only the latest contamination-degree level or shooting control information may be stored in the storage 130 as the contamination-degree information 132. That is, the contamination-degree levels or the shooting control information indicated by the contamination-degree information 132 may be updated each time the sensor controller 122 obtains the contamination-degree level from the contamination sensor 112.

In addition, the method for communication between the devices is not particularly limited to the embodiments described above. When wireless communication is performed between the devices, a system (a communication standard) for the wireless communication is, for example, a short-range wireless communication, such as Zigbee® communication, Bluetooth® communication, or wireless local area network (LAN) communication. Alternatively, the system (a communication standard) for the wireless communication may be communication through a wide-area communication network, such as the Internet. Also, wired communication, instead of the wireless communication, may be performed between the devices. The wired communication is, specifically, power-line communication (PLC), communication using a wired LAN, or the like.

Also, in the embodiments described above, processing executed by a specific processing unit may be executed by another processing unit. The order of the plurality of processings may be changed, or two or more processings may be executed in parallel. In addition, the allocation of the constituent elements included in the purifying system to the devices is one example. For example, any of the constituent elements included in one device may be included in another device. The purifying system may also be implemented as a single device.

For example, the processing described in the above embodiments may be realized by centralized processing using a single device (system) or may be realized by distributed processing using a plurality of devices. The number of processors that execute the program may be one or more. That is, centralized processing may be performed, or distributed processing may be performed.

In the embodiments described above, any or all of the constituent elements, such as the controller, may be implemented by dedicated hardware or may be realized by executing a software program that suits the constituent elements. A program executing unit, such as a central processing unit (CPU) or a processor, may read a software program, recorded in a storage medium, such as a hard disk drive (HDD) or a semiconductor memory, and execute the read software program to thereby realize each constituent element described above.

The constituent elements, such as the controller, may also be implemented by one or more electronic circuits. Each of the electronic circuit(s) may be a general-purpose circuit or may be a dedicated circuit.

The electronic circuit(s) may include, for example, semiconductor devices, integrated circuits (ICs), or large-scale integration (LSI) circuits. The ICs or LSI circuits may be integrated into one chip or may be integrated into a plurality of chips. Although the name used here is an IC or LSI, it may also be called a system LSI, a very-large-scale integration (VLSI), or an ultra-large-scale integration (ULSI) depending on the degree of integration. A field programmable gate array (FPGA) that can be programmed after manufacturing an LSI can also be used for the same purpose.

It should be noted that general or specific embodiments of the present disclosure may be implemented as a system, an apparatus, a device, a method, an integrated circuit, or a computer program. Alternatively, the comprehensive or specific embodiments may be implemented as a computer-readable non-transitory storage medium, such as an optical disc, HDD, or semiconductor memory in which the computer program is stored. In addition, the general or specific embodiments may be implemented as an arbitrary combination of a system, an apparatus, a device, a method, an integrated circuit, a computer program, and a storage medium.

Also, various changes, replacements, additions, and so on within the scope recited in the claims and a scope equivalent thereto can be made to each embodiment described above.

What is claimed is:

1. A purifying method comprising steps of:
    illuminating a measurement area with excitation light;
    detecting fluorescence from the measurement area;
    measuring an amount of amino acids included in the measurement area, based on an intensity of the fluorescence;
    obtaining a contamination-degree level based on the amount of the amino acids included in the measurement area;
    determining an amount of a chemical agent based on the contamination-degree level; and
    discharging the chemical agent to the measurement area, upon determining that the amount of the amino acids exceeds a first threshold, wherein:
    the contamination-degree level comprises three or more levels,
    the amount of the chemical agent is determined such that the higher the contamination-degree level is, the higher the amount of the chemical agent is,
    the method further comprises receiving an instruction for purifying the measurement area, before the chemical agent is discharged, and
    in the step of discharging, upon determining that the contamination-degree level exceeds a second threshold, the chemical agent is discharged to the measurement area regardless of receiving the instruction or not, and upon determining that the contamination-degree level is smaller than or equal to the second threshold, the chemical agent is discharged to the measurement area after receiving the instruction.

2. The purifying method according to claim 1,
    wherein, in the step of discharging, at least one shooting control parameter for discharging the chemical agent is determined by referring to correspondence information in which contamination-degree levels and shooting control parameters are associated with each other.

3. The purifying method according to claim 1,
    wherein, in the step of discharging, a vortex ring formed of gas containing the chemical agent is shot to the measurement area.

4. The purifying method according to claim 1, wherein, in the step of discharging,
    a vortex ring formed of gas containing the chemical agent is shot to the measurement area, and
    at least one shooting control parameter including at least one selected from the group consisting of the number of shoots of the vortex ring, a gas volume of the vortex ring, and a concentration of the chemical agent is adjusted based on the contamination-degree level.

5. The purifying method according to claim 1,
wherein the measurement area is a doorknob or a trace of wiped vomit.

6. The purifying method according to claim 1,
wherein in the step of discharging, the chemical agent is discharged to a local area in the measurement area, and a diameter of the local area is 5 cm or more and 50 cm or less.

7. The purifying method according to claim 1,
wherein, in the step of measuring, the amount of the amino acids is measured based on a combination of a wavelength of the excitation light and a wavelength of the fluorescence.

8. The purifying method according to claim 1, further comprising:
monitoring a user's contact operation on an object included in the measurement area,
wherein, in the step of measuring, after the user finishes the contact operation, the amount of the amino acids in the measurement area is measured.

9. A purifying method comprising steps of:
repeating sequential recording processes, each of which includes
illuminating a measurement area with excitation light, detecting fluorescence from the measurement area,
measuring an amount of amino acids in the measurement area based on an intensity of the fluorescence,
obtaining a contamination-degree level corresponding to the amount of the amino acids, and
recording at least one shooting control parameter corresponding to the obtained contamination-degree level to a storage by using correspondence information in which contamination-degree levels and shooting control parameters for a chemical agent are associated with each other;
obtaining an instruction for purifying the measurement area; and
discharging, after obtaining the instruction, the chemical agent to the measurement area in accordance with the at least one shooting control parameter most recently recorded in the sequential recording processes,
wherein, in the step of repeating the sequential recording processes,
when no instruction is obtained during the step of repeating the sequential recording processes, the chemical agent is not discharged unless the contamination-degree level obtained before the instruction is obtained exceeds a threshold, and
when the contamination-degree level obtained before the instruction is obtained exceeds the threshold, the chemical agent is discharged to the measurement area in accordance with the at least one shooting control parameter most recently recorded in the sequential recording processes.

10. A purifying device comprising:
a discharger that includes a container for storing a chemical agent and that discharges the chemical agent stored in the container; and
a controller that controls the discharger, wherein:
the controller causes the discharger to discharge the chemical agent to a measurement area when an amount of amino acids included in the measurement area exceeds a first threshold,
the amount of the amino acids is measured by a sensor that illuminates the measurement area with excitation light, that detects fluorescence from the measurement area, and that measures the amount of the amino acids based on an intensity of the fluorescence,
the controller determines a contamination-degree level based on the amount of the amino acids and determines an amount of the chemical agent such that the higher the contamination-degree level is, the higher the amount of the chemical agent is,
the contamination-degree level comprises three or more levels,
the controller receives an instruction for purifying the measurement area, before the chemical agent is discharged, and
upon determining that the contamination-degree level exceeds a second threshold, the controller causes the discharger to discharge the chemical agent to the measurement area regardless of receiving the instruction or not, and upon determining that the contamination-degree level is smaller than or equal to the second threshold, the controller causes the discharger to discharge the chemical agent to the measurement area after receiving the instruction.

11. A purifying device comprising:
a discharger that includes a container for storing a chemical agent and that discharges the chemical agent stored in the container;
a controller that controls the discharger; and
a storage,
wherein the controller
repeats sequential recording processes, in each of which the controller obtains a contamination-degree level corresponding to an amount of amino acids included in a measurement area and records at least one shooting control parameter corresponding to the contamination-degree level to the storage by using correspondence information in which contamination-degree levels and shooting control parameters for the chemical agent are associated with each other, the amount of the amino acids being measured by a sensor that illuminates the measurement area with excitation light, that detects fluorescence from the measurement area, and that measures the amount of the amino acids based on an intensity of the fluorescence;
obtains an instruction for purifying the measurement area; and
discharges, after obtaining the instruction, the chemical agent to the measurement area in accordance with the at least one shooting control parameter most recently recorded in the sequential recording processes,
when the controller obtains no instruction during the sequential recording processes, the controller does not discharge the chemical agent unless the contamination-degree level obtained before the instruction is obtained exceeds a threshold, and
when the contamination-degree level obtained before the instruction is obtained exceeds the threshold, the controller discharges the chemical agent to the measurement area in accordance with the at least one shooting control parameter most recently recorded in the sequential recording processes.

12. A purifying system comprising:
a sensor that illuminates a measurement area with excitation light, that detects fluorescence from the measurement area, and that measures an amount of amino acids based on an intensity of the fluorescence; and a purifying device that includes
a discharger that includes a container for storing a chemical agent and that discharges the chemical agent stored in the container, and
a controller that controls the discharger,
wherein the controller causes the discharger to discharge the chemical agent to the measurement area when the amount of the amino acids included in the measurement area exceeds a threshold, the amount of the amino acids being measured by the sensor, and
the controller repeats sequential recording processes, in each of which the controller determines a contamination-degree level based on the amount of the amino acids and determines an amount of the chemical agent such that the higher the contamination-degree level is, the higher the amount of the chemical agent is, and
the controller obtains an instruction for purifying the measurement area before the chemical agent is discharged,
the contamination-degree level comprises three or more levels,
when the controller obtains no instruction during the sequential recording processes, the controller does not discharge the chemical agent unless the contamination-degree level obtained before the instruction is obtained exceeds a threshold, and
when the contamination-degree level obtained before the instruction is obtained exceeds the threshold, the controller discharges the chemical agent to the measurement area in accordance with the at least one shooting control parameter most recently recorded in the sequential recording processes.

13. The purifying system according to claim 12,
wherein the sensor is separated from the purifying device.

* * * * *